United States Patent
Kitamura

(10) Patent No.: US 10,544,309 B2
(45) Date of Patent: *Jan. 28, 2020

(54) PHOTOLUMINESCENT PIGMENT; COSMETIC, PAINT COMPOSITION, AND RESIN COMPOSITION CONTAINING SAME; AND BRIGHT PIGMENT PRODUCTION METHOD

(71) Applicant: Nippon Sheet Glass Company, Limited, Tokyo (JP)

(72) Inventor: Takeaki Kitamura, Sagamihara (JP)

(73) Assignee: Nippon Sheet Glass Company, Limited, Tokyo (JP)

( * ) Notice: Subject to any disclaimer, the term of this patent is extended or adjusted under 35 U.S.C. 154(b) by 943 days.

This patent is subject to a terminal disclaimer.

(21) Appl. No.: 14/363,695

(22) PCT Filed: Dec. 7, 2012

(86) PCT No.: PCT/JP2012/081849
§ 371 (c)(1),
(2) Date: Jun. 6, 2014

(87) PCT Pub. No.: WO2013/085050
PCT Pub. Date: Jun. 13, 2013

(65) Prior Publication Data
US 2014/0349009 A1    Nov. 27, 2014

(30) Foreign Application Priority Data
Dec. 9, 2011   (JP) .................. 2011-270444

(51) Int. Cl.
*C09C 3/06*     (2006.01)
*C09D 5/22*     (2006.01)
(Continued)

(52) U.S. Cl.
CPC ............ *C09C 3/063* (2013.01); *A61K 8/0258* (2013.01); *C03C 17/25* (2013.01); *C08K 9/02* (2013.01);
(Continued)

(58) Field of Classification Search
CPC ......... B05D 5/06; B05D 7/14; C01P 2004/20; C01P 2004/51; C01P 2004/61;
(Continued)

(56) References Cited

U.S. PATENT DOCUMENTS 6,045,914 A    4/2000  Sullivan et al.
7,604,862 B2  10/2009  Ambrosius
(Continued)

FOREIGN PATENT DOCUMENTS

CN    1654548    8/2005
CN    101104748    1/2008
(Continued)

OTHER PUBLICATIONS

Extended European Search Report issued for corresponding European patent application No. 12856041.4, dated Mar. 17, 2017, 4 pages.
(Continued)

*Primary Examiner* — Alexander M Weddle
(74) *Attorney, Agent, or Firm* — Hamre, Schuamnn, Mueller & Larson, P.C.

(57) ABSTRACT

A bright pigment of the present invention is a bright pigment including flaky particles and a metal oxide layer covering each surface of the flaky particles. The metal oxide layer has a thickness variation coefficient (standard deviation of thickness of the metal oxide layer/average thickness of the metal oxide layer) of 20% or less. The bright pigment preferably contains a sodium component, and the sodium component is $Na_2O$. The content of $Na_2O$ in the flaky particles is 3% by
(Continued)

mass or more and less than 9.5% by mass. The bright pigment preferably has a specific surface area of 5.0 m²/g or less.

10 Claims, 1 Drawing Sheet

(51) Int. Cl.
    *C09C 1/00*           (2006.01)
    *C09C 1/40*           (2006.01)
    *C09C 1/28*           (2006.01)
    *C09D 5/36*           (2006.01)
    *A61K 8/02*           (2006.01)
    *C03C 17/25*          (2006.01)
    *C08K 9/02*           (2006.01)
    *B05D 5/06*           (2006.01)
    *B05D 7/14*           (2006.01)

(52) U.S. Cl.
    CPC .......... *C09C 1/0015* (2013.01); *C09C 1/0021* (2013.01); *C09C 1/0081* (2013.01); *C09C 1/28* (2013.01); *C09C 1/40* (2013.01); *C09C 1/405* (2013.01); *C09C 1/407* (2013.01); *C09D 5/22* (2013.01); *C09D 5/36* (2013.01); *A61K 2800/621* (2013.01); *B05D 5/06* (2013.01); *B05D 7/14* (2013.01); *C01P 2004/20* (2013.01); *C01P 2004/51* (2013.01); *C01P 2004/61* (2013.01); *C01P 2006/12* (2013.01); *C01P 2006/60* (2013.01); *C01P 2006/62* (2013.01); *C01P 2006/64* (2013.01); *C01P 2006/65* (2013.01); *C09C 2200/102* (2013.01); *C09C 2200/1004* (2013.01); *C09C 2200/301* (2013.01); *C09C 2200/308* (2013.01); *Y10T 428/258* (2015.01)

(58) Field of Classification Search
    CPC .............. C01P 2006/12; C01P 2006/60; C01P 2006/62; C01P 2006/64; C01P 2006/65; C09C 1/0015; C09C 1/0021; C09C 1/0081; C09C 1/405; C03C 17/25; C08K 9/02
    USPC .................. 106/415, 417; 424/401; 427/212; 524/430
    See application file for complete search history.

(56) References Cited

U.S. PATENT DOCUMENTS

| | | | |
|---|---|---|---|
| 9,683,105 B2 * | 6/2017 | Kitamura ............. | C09D 5/22 |
| 2003/0047115 A1 * | 3/2003 | Bauer .................. | A61Q 1/02 |
| | | | 106/415 |
| 2004/0134385 A1 | 7/2004 | Anselmann et al. | |
| 2004/0166316 A1 | 8/2004 | Noguchi | |
| 2005/0176850 A1 * | 8/2005 | Schmidt ............... | C08K 9/10 |
| | | | 523/160 |
| 2006/0223910 A1 | 10/2006 | Bagala, Sr. | |
| 2006/0225609 A1 | 10/2006 | Rueger et al. | |
| 2007/0032573 A1 | 2/2007 | Yanagase et al. | |
| 2008/0035017 A1 | 2/2008 | Chung | |
| 2009/0274735 A1 | 11/2009 | Wakamiya | |
| 2010/0047300 A1 | 2/2010 | Kaupp | |
| 2010/0083872 A1 | 4/2010 | Kitamura et al. | |
| 2010/0116169 A1 | 5/2010 | Kaupp et al. | |
| 2010/0129412 A1 | 5/2010 | Kitamura | |
| 2010/0297045 A1 | 11/2010 | Kaupp et al. | |
| 2010/0322981 A1 * | 12/2010 | Bujard ................. | C09C 1/0015 |
| | | | 424/401 |
| 2011/0064779 A1 | 3/2011 | Gruener et al. | |
| 2011/0064951 A1 | 3/2011 | Fujiwara et al. | |
| 2011/0151261 A1 | 6/2011 | Fujiwara et al. | |
| 2011/0226161 A1 | 9/2011 | Schumacher et al. | |
| 2011/0251293 A1 | 10/2011 | Trummer et al. | |
| 2016/0168387 A1 | 6/2016 | Shimizu et al. | |

FOREIGN PATENT DOCUMENTS

| | | |
|---|---|---|
| CN | 101404975 | 4/2009 |
| CN | 102026929 | 4/2011 |
| DE | 102004001729 | 8/2005 |
| EP | 0 289 240 | 4/1992 |
| EP | 1 524 305 | 4/2005 |
| EP | 1 564 261 | 8/2005 |
| EP | 1 980 594 | 10/2008 |
| EP | 2 008 641 | 12/2008 |
| JP | 6-240172 | 8/1994 |
| JP | 10-279828 | 10/1998 |
| JP | 2002-509561 | 3/2002 |
| JP | 2002-155241 | 5/2002 |
| JP | 2003-055573 | 2/2003 |
| JP | 2004-168940 | 6/2004 |
| JP | 2005-314649 | 11/2005 |
| JP | 2008-045097 | 2/2006 |
| JP | 2010-031166 | 2/2010 |
| JP | 2010-538096 | 12/2010 |
| WO | 97/46624 | 12/1997 |
| WO | 03/006558 | 1/2003 |
| WO | 2004087816 | 10/2004 |
| WO | 2005/028566 | 3/2005 |
| WO | 2007/054379 | 5/2007 |
| WO | 2007/114442 | 10/2007 |
| WO | 2008/136471 | 11/2008 |
| WO | 2009/037457 A1 | 3/2009 |
| WO | 2009/154064 | 12/2009 |
| WO | 2010/024283 | 3/2010 |

OTHER PUBLICATIONS

European Office Action issued for corresponding European patent application No. 12856041.4, dated Mar. 17, 2017, 4 pages.
Office Action issued in corresponding Japan Application No. 2013-548320, dated Jun. 16, 2016, 3 pages.
Office Action issued in corresponding Japan Application No. 2013-548321, dated Jun. 16, 2016, 2 pages.
Faulkner and Schwartz, "High Performance Pigments, 2nd Ed.", Wiley-VCH Verlag GmbH & Co., KGaA, 2009, pp. 90-94.
Duran Properties, http://www.duran-group.com/de/ueber-duran/duran-eigenschaften.html, retrieved Apr. 18, 2018, 4 pages with an English translation.
Technical data sheet, "ECR Glassflake, milled, Grade GF350nM", Glassflake Ltd., Jun. 2010, v 1.1, 1 page.
Maisch, et al., "Perlglanzpigmente", Verlag Moderne Chemie, 1992, pp. 42-49 along with an English translation.
Technical data sheet, ECR Glassflake, milled, Grade GF100M, Glassflake Ltd., May 2016, 1 page.
Plaff, et al., "Spezielle Effektpigmente", 2007, Vencentz Network, pp. 41-47 along with an English translation.
Notice of Opposition of European Patent Application No. 12855309.6, dated May 2, 2018, 15 pages.
Analytical report, Zeta potential of glass, Dec. 17, 2018 (4 pages).
Pfaff et al., Spezielle Effektpigmente, Vincentz Network, pp. 77-78, 2007, and corresponding English translation.
LA Glass Flake GF001LA, Glassflake Ltd., www.ulprospector.com.
ROEMPP online, keyword "Borosilicatglaser", Apr. 2009, and corresponding English translation.
Material Safety Data Sheet "Low Alkali Glassflake", Glassflake Ltd., Dec. 7, 2017.
Product information "Microglass Glass Flake", GF Europe.
Product information Microglass Glass Flakes, Miihlheimer Grinding, Jun. 12, 2017.
Ullmann's Encyclopedia of Industrial Chemistry, online library, keyword "Glass, 1. Fundamentals", Wiley-VCH Verlag GmbH & Co. KGaA, pp. 1 and 17-28, 2011.
Safety Data Sheet MicroglasR Fineflake MC1080FF, Nippon Sheet Glass Co., Ltd., Jun. 8, 2015.

(56) References Cited

OTHER PUBLICATIONS

Notice of opposition of the European Patent Application No. 12856041, dated Jan. 25, 2019 (15 pages).
Communication from the European Patent Office regarding EP Patent No. 2 789 658, dated Aug. 29, 2019 containing a Letter from the Opponent BASF, dated Aug. 23, 2019, 11 pages.
Safety Data Sheet MicroglasR Fineflake MC108OFF, Nippon Sheet Glass Co., Ltd., Jun. 8, 2015.
Communication from the European Patent Office regarding EP Application No. 12855309.6 dated Oct. 18, 2019 containing a Letter from the Opponent BASF, 44 pages.

* cited by examiner

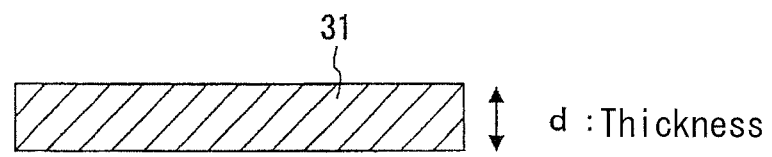
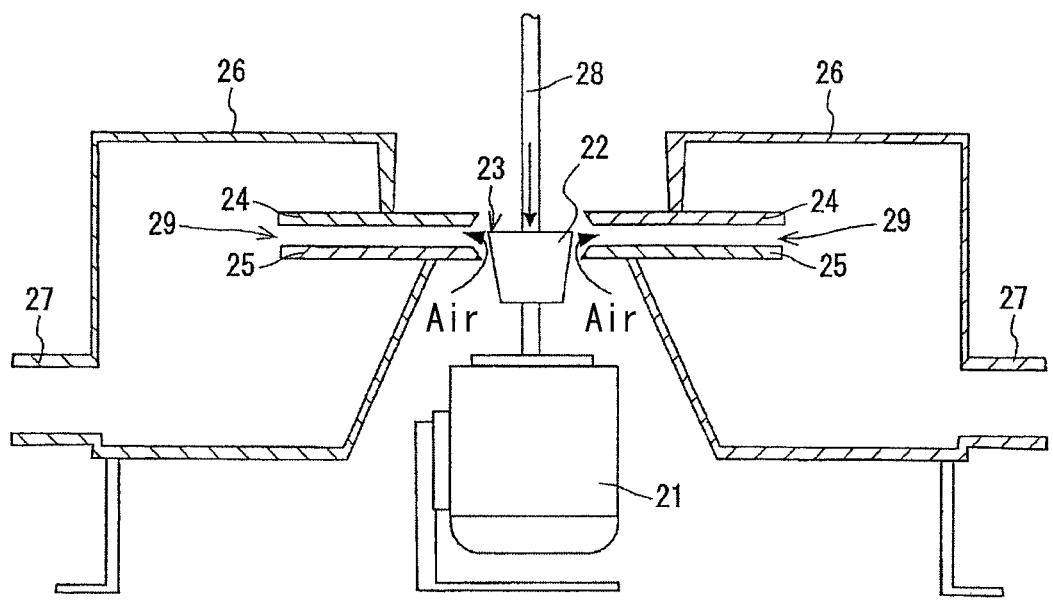
FIG. 1
FIG. 2
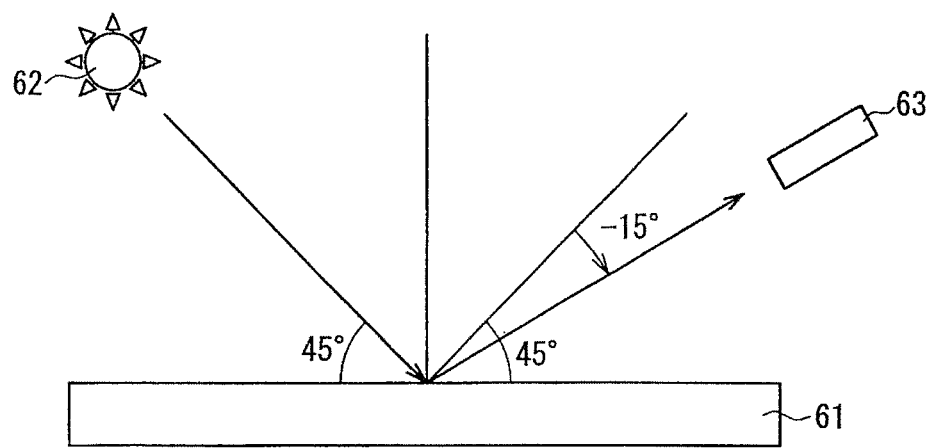
FIG. 3

PHOTOLUMINESCENT PIGMENT; COSMETIC, PAINT COMPOSITION, AND RESIN COMPOSITION CONTAINING SAME; AND BRIGHT PIGMENT PRODUCTION METHOD

TECHNICAL FIELD

The present invention relates to a bright pigment; cosmetics, a paint composition, and a resin composition containing the bright pigment; and a method for producing a bright pigment.

BACKGROUND ART

Conventionally, as a bright pigment such as a pearlescent pigment, a pigment in which each of flaky particles such as mica flakes, synthetic mica flakes, silica flakes, alumina flakes, glass flakes, or graphite flakes is covered with a covering layer containing a metal oxide such as titanium dioxide or iron oxide, iron oxide particles containing α-iron oxide crystals as a main component, and the like have been known. Those pearlescent pigments glitter by reflecting incident light from the outside on surfaces thereof, and impart unique surface appearances that are varying and have beautiful effects to a coating surface when blended with a paint, to a drawn line or a printing surface when blended with ink, or to a surface of a resin molding when blended with a resin composition, together with color tones of various substrate surfaces thereof.

In order to enhance beauty, the pearlescent pigments have been used widely for various applications such as an automobile, a motorcycle, office automation (OA) equipment, a mobile phone, a household electric appliance, various printed matters, and writing instruments.

Titanium dioxide has three kinds of crystal forms including anatase, brookite, and rutile. Of those, anatase and rutile titanium dioxides have been produced industrially. Anatase titanium dioxide has a high photocatalytic activity, and hence accelerates the degradation of components and discoloration of a resin composition and a paint composition. On the other hand, rutile titanium dioxide has a photocatalytic activity that is about one tenth of that of anatase titanium dioxide and is suitable for being blended as a pigment with a resin composition or a paint composition.

JP 2002-509561 A and JP 2010-538096 A propose a pearlescent pigment in which a flaky substrate is covered with a metal oxide layer containing rutile titanium dioxide, as an example of an interference pigment.

PRIOR ART DOCUMENT

Patent Document

Patent document 1: JP 2002-509561 A
Patent document 2: JP 2010-538096 A

DISCLOSURE OF INVENTION

Problem to be Solved by the Invention

However, in the above-mentioned conventional bright pigment such as a pearlescent pigment, both the chromaticness and brightness (luminosity) are low, and hence there is a demand for a bright pigment having higher chromaticness and brightness.

The present invention provides a bright pigment having chromaticness and brightness higher than those of the conventional bright pigments; cosmetics, a paint composition and a resin composition containing the bright pigment; and a method for producing a bright pigment.

Means for Solving Problem

A bright pigment of the present invention includes a flaky particle and a metal oxide layer covering a surface of the flaky particle. The metal oxide layer has a thickness variation coefficient (standard deviation of thickness of the metal oxide layer/average thickness of the metal oxide layer) of 20% or less.

Cosmetics of the present invention include the bright pigment of the present invention.

A paint composition of the present invention includes the bright pigment of the present invention.

A resin composition of the present invention includes the bright pigment of the present invention.

A method for producing a bright pigment of the present invention is a method for producing a bright pigment including a flaky particle and a metal oxide layer covering a surface of the flaky particle. The method includes: a step (step 1) of adding an aqueous solution of a metal compound to a slurry for forming a metal oxide layer containing the flaky particle and acid to deposit a hydrate of an oxide of a metal derived from the metal compound on the surface of the flaky particle, thereby covering the flaky particle with a metal oxide hydrate layer containing the hydrate of the oxide of the metal; and a step (step 2) of washing and drying the flaky particle covered with the metal oxide hydrate layer, and baking the resultant flaky particle covered with the metal oxide hydrate layer to form the metal oxide hydrate layer into a metal oxide layer. The flaky particle to be used for preparing the slurry for forming a metal oxide layer has a zeta potential of −25 mV to −10 mV in hydrochloric acid aqueous solution of pH 2.

Effects of the Invention

The present invention can provide a bright pigment having high brightness and high chromaticness because the thickness variation coefficient of a metal oxide layer covering the surface of a flaky particle is 20% or less. Further, the present invention can provide cosmetics, a paint composition, or a resin composition containing a bright pigment having high brightness and high chromaticness.

BRIEF DESCRIPTION OF DRAWINGS

FIG. 1 is a schematic view showing a thickness "d" of a flaky particle.
FIG. 2 is a partial sectional view schematically showing an example of an apparatus for producing a flaky particle forming a bright pigment of the present invention.
FIG. 3 is a schematic conceptual view illustrating a method for measuring a luminosity L*(−15°).

DESCRIPTION OF THE INVENTION

The inventor of the present invention found that, in a bright pigment including flaky particles and a metal oxide layer covering each surface of the flaky particles, one of the reasons for not obtaining high chromaticness and high brightness lies in the variation in thickness of a metal oxide layer for respective flaky particles. The present invention is based on the finding that a bright pigment having high brightness and high chromaticness is obtained by uniforming the thickness of a metal oxide layer covering each flaky particle and containing a metal oxide layer having a high refractive index for respective flaky particles, that is, by suppressing the variation in thickness of a metal oxide layer.

The degree of variation in thickness of a metal oxide layer can be evaluated based on a thickness variation coefficient of a metal oxide layer described below. As a value of a thickness variation coefficient is smaller, the variation in thickness of a metal oxide layer is smaller. The standard deviation of the thickness of a metal oxide layer and the average thickness of a metal oxide layer are obtained by methods described later in examples.

Thickness variation coefficient of metal oxide layer=
(Standard deviation of thickness of metal oxide layer/average thickness of metal oxide layer)

(Flaky Particle)

The flaky particles have an average thickness of 0.1 μm to 6.0 μm, preferably 0.2 to 2.0 μm, more preferably 0.3 μm to 1.5 μm from the viewpoint of obtaining a bright pigment having high brightness and high chromaticness. The average thickness of the flaky particles is an average value obtained from the result obtained by measuring a thickness "d" (see FIG. 1) of each of any 100 flaky particles with an electron microscope.

The flaky particles are formed of a material having a refractive index of 1.4 to 1.8, preferably 1.5 to 1.6. The flaky particles preferably are formed of an inorganic material, and it is preferred that the flaky particles be formed of one selected from the group consisting of glass, silica, alumina, and mica for the reason that the inorganic material has high transparency with respect to visible light. It is more preferred to use flaky glass particles having high surface smoothness and high transparency, although not particularly limited thereto. In this case, a bright pigment excellent in a single color development property can be provided by covering flaky glass particles with a metal oxide layer containing titanium dioxide and/or iron oxide as main components.

It is preferred that the flaky particles contain a sodium component such as $Na_2O$ in a composition for the reason that a stable electric double layer is formed in the course of production of a bright pigment, and the content of the sodium component is preferably 3% by mass or more and less than 10.5% by mass, more preferably 3% by mass or more and less than 9.5% by mass, still more preferably 3% by mass or more and less than 9% by mass, further preferably 5% by mass or more and less than 9% by mass, still further preferably 7% by mass or more and less than 9% by mass for the reason that a stable electric double layer is formed.

The flaky particles have a particle diameter (D50) corresponding to a 50% volume-cumulative particle diameter from a small particle diameter side, in a particle size distribution, of preferably 10 to 300 μm, more preferably 10 to 200 μm, still more preferably 20 to 150 μm, further preferably 50 to 110 μm for the reason that glittering appearance is enhanced. It should be noted that the thickness of a covering film such as a metal oxide layer is negligibly thin with respect to a particle diameter of the flaky particles.

It should be noted that, in the present specification, the particle diameter of the flaky particles refers to a light scattering nominal diameter obtained by measuring the flaky particles by a laser diffraction/scattering method. For example, according to "Saishin Funtai Bussei Zusetsu (Physical Properties of Powder Particles with Illustrations, Latest Version (3rd edition)" (issued by Yutaka KURATA, published by NGT Co., Jun. 30, 2004), the light scattering nominal diameter is defined as a diameter of a sphere exhibiting a scattering pattern closest to a light scattering pattern of a particle obtained by measurement and having the same refractive index as that of the particle.

Further, the particle size distribution is an index indicating which size (particle diameter) of particles are contained in which ratio in a group of particles to be measured, and in the present specification, the particle size distribution is measured by the laser diffraction/scattering method. The laser diffraction/scattering method is a method for determining a particle size distribution through use of scattered light obtained when particles are irradiated with light, and in the particle size distribution in the present specification, a volume is used as a reference of a particle amount. The maximum particle diameter refers to a particle diameter corresponding to a 100% volume-cumulative particle diameter in a particle size distribution.

The flaky glass particles may be produced, for example, by producing a thin glass film through use of a flow of molten glass caused by a centrifugal force and crushing the glass film. FIG. 2 shows an example of an apparatus for producing flaky glass particles through use of a flow of molten glass. The apparatus includes a tapered cup 22 attached to a variable-speed electric motor 21, and a rim 23 of the cup 22 is positioned between two annular plates 24, 25. An upper plate 24 is provided so as to move vertically, and the distance between the plates 24, 25 can be regulated. The plates 24, 25 are attached inside a cyclone-type vacuum chamber 26, and the chamber 26 is connected to a cyclone collection/separation/vacuum pump (not shown) via an outlet connection 27. The cup 22 is rotated at a predetermined speed, and molten glass 28 is poured into the cap 22 from above. The molten glass in the cup 22 is sent outside beyond the rim 23 due to the centrifugal force. The pressure inside the chamber 26 is lowered by operating the cyclone collection-separation-vacuum pump, and air enters the chamber 26 through a region 29 between the plates 24, 25. The air having entered the chamber 26 quenches the molten glass sent outside beyond the rim 23 of the cup 22. Further, an airflow flowing between the plates 24, 25 also has a function of holding the molten glass so that the molten glass sent beyond the rim 23 of the cup 22 and positioned between the plates 24, 25 does not come into contact with the surfaces of the plates 24, 25. The airflow between the plates 24, 25 cools the molten glass between the plates 24, 25 until the molten glass becomes a solid. The glass positioned between the plates 24, 25 is pulled out in a radial direction due to the friction with the airflow and crushed into small flake-shaped glass while being kept in a plate shape by the airflow. The flaky glass particles thus obtained are collected in the chamber 26 and sent to a cyclone collection/filtration section (not shown) through the outlet connection 27.

In the case of producing flaky glass particles through use of the apparatus, the thickness of the flaky glass particles can be regulated by regulating the distance between the plates 24, 25, the speed of the airflow between the plates 24, 25, and the like.

A preferred example of a composition of the flaky particles to be used for producing a bright pigment is described below.

TABLE 1

Composition of flaky synthetic mica particles

|  | Reference example Fluorine gold mica $KMg_3(AlSi_3O_{10})F_2$ | Reference example Potassium tetrasilicon mica $KMg_{2.5}(Si_4O_{10})F_2$ | Example of present invention Sodium tetrasilicon mica $NaMg_{2.5}(Si_4O_{10})F_2$ |
|---|---|---|---|
| $SiO_2$ | 40-50 | 53-65 | 55-65 |
| $Al_2O_3$ | 6-15 | — | — |
| MgO | 25-35 | 20-28 | 21-29 |
| $Na_2O$ | — | — | 4-9 |
| $K_2O$ | 5-10 | 7-13 | — |
| F | 5-13 | 7-14 | 6-15 |

(Unit: % by mass)

TABLE 2

Composition of flaky alumina particles

|  | Example of present invention | Reference example | Reference example |
|---|---|---|---|
| $Al_2O_3$ | 92.8 | 97.9 | 78.5 |
| $Na_2O$ | 4.2 | 0.1 | 1.3 |
| $K_2O$ | 2 | — | 17.4 |
| $TiO_2$ | — | 0.8 | 1 |
| $P_2O_5$ | 1 | 1.2 | 1.8 |

(Unit: % by mass)

TABLE 3

Composition of flaky glass particles

|  | Example of present invention | A glass | C glass | ECR glass | WO2006/ 068255 |
|---|---|---|---|---|---|
| $SiO_2$ | 59-69 | 70-73 | 65-70 | 55-60 | 60-65 |
| $Al_2O_3$ | 2-12 | 1.0-1.8 | 1-7 | 9-13 | 8-12 |
| CaO | 5-18 | 7-12 | 4-11 | 15-25 | 20-24 |
| MgO | 0-5 | 1.0-4.5 | 0-5 | 1-5 | 1-5 |
| $B_2O_3$ | 0-7 | — | 0-8 | — | — |
| $Na_2O$ | 3-9 | 10-13 | 9-14 | 0-2 | 0-2 |
| $K_2O$ | 0-1 | 0-3 | 0-3 | 0-1 | 0-1 |
| ZnO | 0-2 | — | 0-6 | 1-5 | — |
| $TiO_2$ | — | — | — | 1-5 | 0-5 |
| $FeO/Fe_2O_3$ | — | 0-0.2 | — | — | — |

(Unit: % by mass)

(Classification Method)

In the present invention, the particle size of flaky particles can be adjusted by, for example, sieve classification. For example, a dry-type vibrating sieving machine can be used for sieve classification. It is appropriate that the mesh size of a sieve to be used is selected appropriately depending on the particle size of the flaky particles before sieving or the target particle diameter of the flaky particles.

Further, a classification method other than the sieve classification may be used in order to remove fine powder and coarse powder.

In the case of dry classification, an airflow classifier such as a gravitational classifier, an inertial classifier, and a centrifugal classifier can be used for removing coarse powder. As a gravitational classifier, horizontal flow-type, vertical flow-type, and inclined flow-type classifiers, for example, can be used. As an inertial classifier, linear-type, curving-type, and louver-type classifiers, an Elbow-Jet, and a Variable Impactor, for example, can be used. As a centrifugal classifier using air vortex, cyclone-type, Vantongeren-type, and classiclone-type classifiers, a Dispersion Separator, and a Microplex can be used. As a centrifugal classifier using mechanical rotation, a Micron Separator, a Turboplex, an Acucut, a Turbo Classifier, and the like can be used.

In the case of wet classification, an airflow classifier such as a gravitational classifier and a centrifugal classifier can be used. As a gravitational classifier using gravity settling tanks, a settling tank, a deposition cone, a Spitzkasten, and a Hydroseparator can be used. As a gravitational classifier using mechanical rotation, a drag chain classifier, a rake classifier, a ball classifier, a spiral classifier and the like can be used. As a hydraulic classifier, a "doruko" sizer, a Valenwald sizer, a syphon sizer, a hydroscillator, and the like can be used. As a centrifugal classifier, hydrocyclone and centrifugal classifiers (disk-type and decanter-type) and the like can be used.

(Metal Oxide Layer)

A specific example of the metal oxide layer is described below.

It is preferred that a metal oxide contained in a metal oxide layer covering a flaky particle be at least one metal oxide selected from the group consisting of titanium dioxide ($TiO_2$), reduced titanium oxide ($TiO_{2-x}$), iron oxide ($Fe_2O_3$), and reduced iron oxide ($Fe_3O_4$) for the reason that a metal oxide layer having a high refractive index is likely to be formed, and the weather resistance of a bright pigment is satisfactory with the number of active points of a photo-catalyst being small. It should be noted that reduced titanium oxide is obtained by reducing titanium oxide in an atmosphere containing hydrogen at 400° C. to 600° C., and reduced iron oxide is obtained by reducing iron oxide in an atmosphere containing hydrogen at 400° C. to 600° C.

<Titanium Dioxide Layer>

As an example of the metal oxide layer covering each flaky particle, there is given a titanium dioxide layer. It is appropriate that the titanium dioxide layer covering each flaky particle is substantially composed of rutile titanium dioxide. When rutile titanium dioxide is used as a metal oxide, a bright pigment having high brightness and high chromaticness is obtained because the metal oxide contains dense crystals having a small specific surface area and has high density, that is, a metal oxide layer has a high refractive index. Herein, the term "substantially" means that the amount of components other than titanium dioxide in the metal oxide layer is 0.1% by mass or less, preferably 0.01% by mass or less. Examples of the components other than titanium dioxide include $SnO_2$ and $Na_2O$.

Titanium dioxide has three kinds of crystal forms such as anatase, brookite, and rutile. Of those, anatase and rutile titanium dioxides have been produced industrially. Anatase titanium dioxide has a high photocatalytic activity, and hence accelerates the degradation and discoloration of a resin and a paint. On the other hand, rutile titanium dioxide has a photocatalytic activity that is about one tenth of that of anatase titanium dioxide, and flaky particles covered with rutile titanium dioxide are suitable for being used as a pigment in a paint composition or a resin composition. Further, rutile titanium dioxide has a refractive index higher than that of anatase titanium dioxide and can easily form a dense and uniform covering film, and hence enhances a color development property due to the interference of light. As a method for producing a rutile titanium dioxide layer, there can be illustrated a method for depositing a hydrate of rutile titanium dioxide from a titanium-containing solution by a neutralization reaction under conditions of a temperature of 55° C. to 85° C. and a pH of 1.3 or less, as disclosed by JP 2001-31421 A. According to this method, heating for crystal form transformation is not basically required, and rutile titanium dioxide also can be easily fixed on a base (flaky particle) having low heat resistance. The thickness of a rutile titanium dioxide layer is preferably 20 nm to 350 nm, more preferably 30 nm to 300 nm, still more preferably 40 nm to 250 nm for the reason that the brightness by light reflection and an optical path difference sufficient for interference are obtained.

<Reduced Titanium Oxide Layer>

As another example of the metal oxide layer covering each flaky particle, there is given a reduced titanium oxide layer. A bright pigment in which flaky particles are covered with a reduced titanium oxide layer is obtained by reducing flaky particles covered with a titanium dioxide layer in an atmosphere containing hydrogen at 400° C. to 600° C.

<Iron Oxide Layer>

As another example of the metal oxide layer covering each flaky particle, there is given an iron oxide layer. Iron oxide has a low photocatalytic activity that is about one tenth of that of anatase titanium dioxide in the same manner as rutile titanium dioxide, and flaky particles covered with iron oxide are suitable for being used as a pigment in a paint composition or a resin composition. The use of iron oxide can realize coloration of chromatic colors developed by absorption of light by iron oxide and colors (bronze color, orange color, red color) developed by interference of light, which are overlapped with each other. As iron oxide covering a flaky particle, a trivalent iron oxide, or a mixture of a bivalent iron oxide and a trivalent iron oxide can be used. It is appropriate that the iron oxide layer covering each flaky particle is substantially formed of the above-mentioned iron oxide. Herein, the term "substantially" means that the amount of components other than iron oxide in the metal oxide layer is 0.1% by mass or less, preferably 0.01% by mass or less. Examples of the components other than iron oxide include $SnO_2$ and $Na_2O$.

As a method for producing an iron oxide layer, there can be illustrated a method for depositing a hydrate of iron oxide on the surface of each flaky particle from an iron-containing solution by a neutralization reaction under conditions of a temperature of 50° C. to 80° C. and a pH of 2 to 4, as disclosed by JP 2005-187782 A. The thickness of an iron oxide layer is preferably 20 nm to 350 nm, more preferably 30 nm to 300 nm, still more preferably 40 nm to 250 nm for the reason that the brightness by light reflection and an optical path difference sufficient for interference are obtained.

<Reduced Iron Oxide Layer>

As another example of the metal oxide layer covering each flaky particle, there is given a reduced iron oxide layer. A bright pigment in which flaky particles are covered with a reduced iron oxide layer is obtained by reducing flaky particles covered with an iron oxide layer in an atmosphere containing hydrogen at 400° C. to 600° C.

In order to obtain a bright pigment having high brightness and high chromaticness, it is important that the thickness of a metal oxide layer containing titanium dioxide, iron oxide, or the like covering each flaky particle as a main component is uniformed for respective flaky particles. When the thickness of the metal oxide layer varies depending on the flaky particle, brightness and chromaticness are degraded. Thus, in the present invention, the thickness variation coefficient (standard deviation of thickness of metal oxide layer/average thickness of metal oxide layer) of the metal oxide layer is preferably 20% or less, more preferably 10% or less. still more preferably 8% or less from the viewpoint of enhancing brightness and chromaticness.

A liquid phase deposition (LPD) method is preferred as the method for forming a metal oxide layer. Then, in order to make uniform the thickness of a metal oxide layer containing rutile titanium dioxide, iron oxide, or the like serving as a high refractive index material as a main component, it is desired that the zeta potential of the flaky particles be set to be a negative potential. Rutile titanium oxide or iron oxide can be deposited by adjusting the concentration of chlorine in a reaction solution containing an acid such as hydrochloric acid. It is preferred that the pH of a reaction solution be lower than an isoelectric point of a metal oxide. The isoelectric point of rutile titanium oxide is pH 4.5, and that of iron oxide is 9.5.

According to the liquid phase deposition method, an aqueous solution of a metal compound is added to a slurry (slurry for forming a metal oxide layer) obtained by soaking flaky particles in an aqueous solution of an acid such as hydrochloric acid, and a hydrate layer of an oxide of a metal derived from the metal compound is formed on the flaky particles. The pH of the slurry and the pH of a mixture (reaction solution) of the slurry and the aqueous solution of a metal compound is preferably 1.3 or less, more preferably 0.9 to 1.2 in the case where the metal oxide is titanium dioxide, and is preferably 2.0 to 4.0, more preferably 2.5 to 3.5 in the case where the metal oxide is iron oxide.

It is preferred that the composition of the flaky particles contain a sodium component for the following reason. In a slurry, sodium diffuses from inside of a flaky particle to a surface layer, with the result that an electric double layer is formed at an interface between the flaky particle and the liquid. Then, the concentration of sodium on the surface of the flaky particle increases. In the case where a metal oxide is titanium dioxide and an aqueous solution of a metal compound is an aqueous solution of titanium tetrachloride, hydrolysis of titanium tetrachloride (metal compound aqueous solution) occurs, with the result that a hydrate layer of titanium dioxide is formed selectively on the surface of the flaky particle. In the case where a metal oxide is iron oxide, and an aqueous solution of a metal compound is an aqueous solution of iron chloride, hydrolysis of iron chloride (metal compound aqueous solution) occurs, with the result that a hydrate layer of iron oxide is formed selectively on the surface of the flaky particle.

For example, in the case where the zeta potential of flaky particles to be used for producing a bright pigment in hydrochloric acid aqueous solution of pH 2 is −25 mV to −10 mV, a stable electric double layer can be formed. The zeta potential is preferably −25 mV to −15 mV, more preferably −25 mV to −18 mV from the viewpoint of forming a stable electric double layer. In order to realize a zeta potential of −25 mV to −10 mV, preferably −25 mV to −15 mV, more preferably −25 mV to −18 mV, it is preferred that the flaky particles contain a sodium component (for example, $Na_2O$), and the content of $Na_2O$ in the flaky particles is preferably 3% by mass or more and less than 10.5% by mass, more preferably 3% by mass or more and less than 9.5% by mass, still more preferably 3% by mass or more and less than 9% by mass, further preferably 5% by mass or more and less than 9% by mass. In other words, the concentration of Na in the flaky particles is preferably 3% by mass or more and less than 10.5% by mass, more preferably 3% by mass or more and less than 9.5% by mass, still more preferably 3% by mass or more and less than 9% by mass, further preferably 5% by mass or more and less than 9% by mass, in terms of $Na_2O$.

In the case where the metal oxide layer is a titanium dioxide layer or a reduced titanium oxide layer, as an aqueous solution of a metal compound that is a material from which the metal oxide layer is derived, there is given an aqueous solution containing at least one kind of a metal compound selected from the group consisting of titanium tetrachloride, titanium trichloride, titanium dichloride, titanium sulfate, titanyl sulfate, titanium nitrate, and titanyl nitrate. From the viewpoint of forming a rutile crystal phase, an aqueous solution containing at least one kind of a metal compound selected from the group consisting of titanium tetrachloride, titanium trichloride, and titanium dichloride is preferred, and an aqueous solution of titanium tetrachloride is more preferred.

In the case of forming a layer substantially made of titanium dioxide on the surface of each flaky particle, the temperature of a slurry in which flaky particles are dispersed in an aqueous solution of an acid such as hydrochloric acid (slurry for forming a metal oxide layer) immediately before and while being mixed with an aqueous solution of a metal compound is kept at preferably 60° C. to 85°, more preferably 70° C. to 80° C. in the liquid phase deposition method.

On the other hand, in the case of forming a layer substantially made of iron oxide on the surface of each flaky particle, for forming a layer substantially made of a hydrate of iron oxide on the surface of each flaky particle, the temperature of a slurry in which flaky particles are dispersed in an aqueous solution of an acid such as hydrochloric acid (slurry for forming a metal oxide layer) immediately before and while being mixed with an aqueous solution of a metal compound is kept at preferably 50° C. to 80° C. in the liquid phase deposition method.

Thus, in order to make uniform the thickness of a metal oxide layer covering a flaky particle, it is necessary to create conditions under which a hydrate of a metal oxide is likely to be deposited, depending on the kind of the metal oxide and the material for flaky particles.

In the present invention, in an acidic slurry containing chlorine ions and a reaction solution, sodium contained in flaky particles as an oxide diffuses from an inside of each flaky particle to the surface thereof, with the result that an electric double layer is formed at an interface between the flaky particle and the liquid. The zeta surface potential of each flaky particle becomes negative, and hydrolysis of titanium tetrachloride (metal compound) occurs in the vicinity of the surface of the flaky particle, and a hydrate of rutile titanium dioxide is selectively deposited on the surface of the flaky particle. The flaky particles each covered with a hydrate layer of rutile titanium dioxide are subjected to washing, drying, and baking to become a bright pigment in which each of the flaky particles is covered with a metal oxide layer containing rutile titanium dioxide as a main component. In the foregoing reaction system, the covering speed of a hydrate of rutile titanium dioxide proceeds quantitatively, and the occurrence of thickness unevenness of a metal oxide layer is suppressed, and the occurrence of thickness unevenness of metal oxide layers among flaky particles is also suppressed. It should be noted that the "metal oxide layer containing rutile titanium dioxide as a main component" means that a main component forming a metal oxide layer is rutile titanium dioxide, and that a metal oxide layer is substantially formed of rutile titanium dioxide. Herein, the term "substantially" means that components other than a desired metal oxide, such as a catalyst, is contained in a metal oxide layer irreversibly in the course of formation of the metal oxide layer, and the contents of the components other than the desired metal oxide in the metal oxide layer is 0.1% by mass or less, preferably 0.01% by mass or less.

Further, in the case where sodium is taken in a crystal phase, the dehydration and condensation reaction of rutile titanium dioxide is accelerated, and hence a metal oxide hydrate layer substantially formed of a hydrate of rutile titanium oxide having a small number of pores and high density is obtained. Further, the crystallization degree is enhanced by baking at low temperature (600° C. or less), and titanium dioxide particles do not become enlarged. In the thus obtained metal oxide layer containing rutile titanium dioxide as a main component, covering the surface of a flaky particle, dense crystals having a small specific surface area are obtained, and hence a bright pigment having high density of the metal oxide layer, that is, a high refractive index and having high brightness and high chromaticness is obtained.

Further, the covering thickness of rutile titanium dioxide is made uniform for respective bright pigments, and hence the uniformity of interference light is increased and a bright pigment having high brightness and high chromaticness is obtained.

In the case of covering each flaky particle with a hydrate layer of titanium dioxide, it is preferred that flaky particles in a slurry obtained by adding the flaky particles to an acidic aqueous solution be treated in advance with tin oxide serving as a surface reforming agent by, for example, the following method.

Hydrochloric acid aqueous solution with stannic chloride dissolved therein is added in a predetermined amount to a slurry containing flaky particles. After that, the resultant slurry is allowed to stand, whereby the surface of the flaky particles can be treated (covered) with tin oxide. The addition amount of hydrochloric acid aqueous solution with stannic chloride dissolved therein to the slurry may be determined appropriately depending on the mass, thickness (surface area of flaky particles), and the like of the flaky particles.

The pH of the slurry before the addition of tin oxide is preferably 1.5 to 2.0, more preferably 1.5 to 1.8 for the reason that the flaky particles are covered uniformly with tin oxide.

As described above, a preferred example of a method for producing a bright pigment of the present invention includes: a deposition step (step 1) of adding an aqueous solution of a metal compound to a slurry for forming a metal oxide layer obtained by adding tin as necessary to a slurry containing flaky particles, hydrochloric acid, and water to deposit a hydrate of an oxide of a metal derived from the metal compound on the surface of the flaky particles; and a step (step 2) of collecting the flaky particles on each surface of which a hydrate layer of the metal oxide is formed from a mixture of the slurry for forming a metal oxide layer and an aqueous solution of a metal compound after the deposition step, and then, washing, drying, and baking the flaky particles to form a bright pigment containing the flaky particles and a metal oxide layer covering each flaky particle.

In the above-mentioned production method, the drying temperature is preferably 150° C. to 250° C. The baking temperature is preferably 400° C. to 700° C., more preferably 550° C. to 650° C. from the viewpoint of enhancing the crystallization degree of a metal oxide and preventing the enlargement of crystals. It should be noted that the drying temperature or the baking temperature is respectively atmospheric temperature in a drier or a baking furnace, and respectively can be checked through a temperature display section of the drier or the baking furnace.

In the above-mentioned step 1, in the case where the metal oxide is at least one kind selected from titanium dioxide and reduced titanium oxide, the aqueous solution of a metal compound is added to the slurry for forming a metal oxide layer while keeping the pH of the mixture of the slurry for forming a metal oxide layer and the aqueous solution of a metal compound at, for example, 0.9 to 1.2 by a basic aqueous solution. Further, in the step 1, in the case where the metal oxide is at least one kind selected from iron oxide and reduced iron oxide, the aqueous solution of a metal compound is added to the slurry for forming a metal oxide layer while keeping the pH of the mixture of the slurry for forming a metal oxide layer and the aqueous solution of a metal compound at, for example, 2.0 to 4.0 using a basic aqueous solution.

As the basic aqueous solution, an aqueous solution of sodium hydroxide, lithium hydroxide, potassium hydroxide, or ammonia can be used.

The specific surface area of the bright pigment of the present invention produced by a preferred example of the method for producing a bright pigment of the present invention is preferably 5.0 $m^2/g$ or less, more preferably 3.0 $m^2/g$ or less, still more preferably 2.5 $m^2/g$ or less from the viewpoint of increasing a refractive index and enhancing brightness and chromaticness.

Next, examples of cosmetics, cosmetics, a paint composition, and a resin composition containing the bright pigment of the present embodiment are described.

[Cosmetics]

Next, an example of cosmetics containing an example of the bright pigment of the present invention is described. The cosmetics include a wide range of cosmetics such as facial cosmetics, makeup cosmetics, and hair cosmetics. Of those, in particular, in makeup cosmetics such as foundation, face powder, eye shadow, blusher, foundation cream, nail enamel, eye liner, mascara, lipstick, and fancy powder, the bright pigment of the present embodiment is preferably used.

Depending on the purpose of cosmetics, the bright pigment of the present embodiment may be appropriately subjected to a hydrophobization treatment. As the hydrophobization treatment, there are given the following five methods.

(1) A treatment method using a silicone compound such as methyl hydrogen polysiloxane, high-viscosity silicone oil, or a silicone resin (2) A treatment method using a surfactant such as an anionic activator or a cationic activator (3) A treatment method using a polymer compound such as nylon, polymethyl methacrylate, polyethylene, various fluorine resins (polytetrafluoroethylene resin (PTFE), tetrafluoroethylene perfluoroalkyl vinyl ether copolymer (PFA), a tetrafluoroethylene hexafluoropropylene copolymer (FEP), an ethylene-tetrafluoroethylene copolymer (ETFE), polyvinylidene fluoride (PVDF), polychlorotrifluoroethylene (PCTFE), etc.), or polyamino acid (4) A treatment method using a perfluoro group-containing compound, lecithin, collagen, metallic soap, lipophilic wax, or a polyhydric alcohol partial ester/complete ester (5) A treatment method obtained by combining the above-mentioned methods It should be noted that methods other than the above-mentioned methods also can be used as long as they can be generally applied to a hydrophobization treatment of powder.

Further, other materials generally used for cosmetics can be blended appropriately as needed with the above-mentioned cosmetics. Examples of the other materials include inorganic powder, organic powder, pigments other than the bright pigment of the present invention, a dye, a coloring matter, oils and fats, an organic solvent, a resin, a plasticizer, an ultraviolet absorber, an antioxidant, an antiseptic agent, a surfactant, a moisturizing agent, perfume, water, alcohol, and a thickener.

Examples of the inorganic powder include talc, kaolin, sericite, white mica, gold mica, lepidolite, black mica, lithia mica, vermiculite, magnesium carbonate, calcium carbonate, diatomaceous earth, magnesium silicate, calcium silicate, aluminum silicate, barium sulfate, tungstate metal salt, silica, hydroxyapatite, zeolite, boron nitride, and ceramics powder.

Examples of the organic powder include nylon powder, polyethylene powder, polystyrene powder, benzoguanamine powder, polytetrafluoroethylene powder, distyrenebenzene polymer powder, epoxy powder, acrylic powder, and microcrystalline cellulose.

The pigment is roughly classified into an inorganic pigment and an organic pigment. Examples of the inorganic pigment include the following on the basis of various colors.
Inorganic white pigment: titanium oxide, zinc oxide, etc.
Inorganic red pigment: iron oxide (colcothar), iron titanate, etc.
Inorganic brown pigment: γ-iron oxide, etc.
Inorganic yellow pigment: yellow iron oxide, loess, etc.
Inorganic high-chromaticness pigment: black iron oxide, carbon black, etc.
Inorganic purple pigment: mango violet, cobalt violet, etc.
Inorganic green pigment: cobalt titanate, etc.
Inorganic blue pigment: navy blue, indigo blue, etc.

Further, examples of the pearlescent pigment include mica coated with titanium oxide, bismuth oxychloride coated with titanium oxide, bismuth oxychloride, talc coated with titanium oxide, argentine, and colored mica coated with titanium oxide. Further, examples of the metal powder pigment include aluminum powder and copper powder.

As the organic pigment, there are given the following (1) and (2).

(1) Red No. 201, Red No. 202, Red No. 204, Red No. 205, Red No. 220, Red No. 226, Red No. 228, Red No. 405, Orange No. 203, Orange No. 204, Yellow No. 205, Yellow No. 401, Blue No. 404, and the like defined as certified coloring matters, serving as tar dye that can be used for medicines approved by Ministry of Health, Labor, and Welfare of Japan (2) Organic pigments obtained by laking dyes listed below into extender pigments such as talc, calcium carbonate, barium sulfate, zirconium oxide, or aluminum white Examples of the dye include Red No. 3, Red No. 104, Red No. 106, Red No. 227, Red No. 230, Red No. 401, Red No. 505, Orange No. 205, Yellow No. 4, Yellow No. 5, Yellow No. 202, Yellow No. 203, Green No. 3, and Blue No. 1 defined as certified coloring matters.

Further, examples of the coloring matter include natural coloring matters such as chlorophyll and β-carotin.

Further, examples of the oils and fats include squalane, (hydrogenated) polybutene, liquid paraffin, Vaseline, microcrystalline wax, ozokerite, ceresin, myristic acid, palmitic acid, stearic acid, oleic acid, isostearic acid, cetyl alcohol, hexadecyl alcohol, oleyl alcohol, cetyl 2-ethylhexanoate, palmitic acid 2-ethylhexyl, 2-octyldodecyl myristate, neopentyl glycol di-2-ethylhexanoate, glycerol tri-2-ethylhexanoate, 2-octyldodecyl oleate, isopropyl myristate, glycerol triisostearate, glycerol tricocoate, olive oil, avocado oil, bees wax, myristyl myristate, mink oil, and lanoline.

Further, examples of the organic solvent include acetone, toluene, butyl acetate, or acetic acid ester; examples of the resin include an alkyd resin or a urea resin; and examples of the plasticizer include camphor or acetyltributyl citrate.

The form of the cosmetics is not particularly limited, and examples thereof include a powdery form, a cake form, a pencil form, a stick form, an ointment form, a liquid form, an emulsion form, and a cream form.

[Resin Composition]

Next, an example of a resin composition containing an example of the bright pigment of the present invention is described. Examples of a molding to be molded through use of the resin composition of the present embodiment include containers for cosmetics, food containers, coating materials, floor materials, housings of household electric appliances, accessories, stationery, toys, bathtubs, bath goods, footwear, sports goods, and toilet goods. The resin composition of the present embodiment contains an example of the bright pigment of the present invention and a base material resin.

Examples of the base material resin include thermosetting resins such as a polycarbonate resin, an acrylic resin, a polyester resin, an epoxy resin, a phenol resin, a urea resin, a fluorine resin, a polyester-urethane curable resin, an epoxy-polyester curable resin, an acrylic polyester based resin, an acrylic urethane curable resin, an acrylic melamine curable resin, and a polyester-melamine curable resin; and thermoplastic resins such as a polyethylene resin, a polypropylene resin, a petroleum resin, a thermoplastic polyester resin, and a thermoplastic fluorine resin. In the case of using a thermoplastic resin as a base material resin, injection molding can be performed, and a molding having a complicated shape can be molded. Flaky particles of a bright pigment are preferably glass not having the cleavage property found in mica, by which glass can keep a particle diameter before molding even after being subjected to injection molding.

The resin composition of the present embodiment may contain a curing agent as needed. Examples of the curing agent include polyisocyanate, amine, polyamide, polybasic acid, acid anhydride, polysulfide, boron trifluoride, acid dihydrazide, and imidazole.

The resin composition of the present embodiment further may contain a pigment other than the bright pigment of the present invention, a surfactant, a lubricant, a defoaming agent, and a leveling agent.

The content of each component in the resin composition is not limited in the present invention and may be similar to that of the conventionally known resin composition.

[Paint Composition]

Next, an example of a paint composition containing an example of the bright pigment of the present invention is described. The paint composition of the present embodiment can be produced by mixing the bright pigment of the present embodiment described above with a vehicle. The vehicle is formed of an aqueous resin composition containing an aqueous emulsion resin and a cross-linking curing agent, and other additives, described below.

<Aqueous Resin Composition>

(Aqueous Emulsion Resin)

An aqueous emulsion resin is obtained by subjecting a polymerizable unsaturated monomer having a carbonyl group described below to emulsion polymerization in the presence of an emulsifier. Examples of the emulsifier include an anionic surfactant and a nonionic surfactant, and the aqueous emulsion resin is obtained by emulsion polymerization through use of a polymerization initiator such as a persulfate and a peroxide in the presence of one or two or more kinds of the emulsifiers.

(Polymerizable Unsaturated Monomer Having a Carbonyl Group)

The above-mentioned polymerizable unsaturated monomer having a carbonyl group is selected from the following (a) to (d).

(a) The polymerizable unsaturated monomer having a carbonyl group is, for example, a polymerizable unsaturated monomer having at least one carbonyl group in one molecule, and more specifically, for example, there are given diacetone acrylamide and diacetone methacrylamide.

(b) The polymerizable unsaturated monomer having a carbonyl group is, for example, a polyfunctional vinyl compound having at least two polymerizable unsaturated bonds in one molecule, and includes a polymerizable unsaturated monocarboxylic acid ester of polyhydric alcohol, a polymerizable unsaturated alcohol ester of a polybasic acid, and an aromatic compound substituted by two or more vinyl groups. More specifically, for example, there are given allyl(meth)acrylate, ethylene glycol di(meth)acrylate, triethylene glycol di(meth)acrylate, and tetraethylene glycol di(meth)acrylate.

(c) The polymerizable unsaturated monomer having a carbonyl group is, for example, a water-soluble ethylenically unsaturated monomer. More specifically, as an anion-based monomer, there are given, for example, (meth)acrylic acid, maleic acid, crotonic acid, β-carboxyethyl acrylate, and the like; as a cation-based monomer, there are given (meth) acrylamide, dimethylaminopropyl(meth)acrylamide, dimethylaminoethyl(meth)acrylate, and the like; and as a non-ion-based monomer, there are given (meth)acrylate having a polyoxyethylene chain and the like.

(d) The polymerizable unsaturated monomer having a carbonyl group is, for example, other ethylenically unsaturated monomers. More specifically, for example, there are given methyl(meth)acrylate, ethyl(meth)acrylate, propyl (meth)acrylate, butyl(meth)acrylate, 2-ethylhexyl(meth) acrylate, cyclohexyl(meth)acrylate, and lauryl(meth)acrylate.

(Cross-Linking Curing Agent)

As a cross-linking curing agent, for example, there is given a hydrazide compound having at least two hydrazide groups per molecule. More specifically, for example, there are given dihydrazide oxalate, dihydrazide malonate, dihydrazide succinate, dihydrazide glutarate, and dihydrazide adipate.

<Other Additives>

The paint composition may contain the following other additives depending on the application thereof. Examples of the other additives include thermoplastic resins (for example, a vinyl chloride resin free of a carbonyl group, a polyethylene resin free of a carbonyl group, etc.), thermosetting resins (for example, an urethane resin, an amino resin, etc.), antioxidants, ultraviolet absorbers, stabilizers such as heat stabilizers, plasticizers, antistatic agents, dispersants, antiskinning agents, viscosity modifiers such as thickeners, planarizers, antidripping agents, fungicides, preservatives, fillers, dyes and pigments (such as phthalocyanine pigment, perylene pigment, quinacridone pigment, indigo pigment, isoindolinone pigment, colcothar, yellow iron oxide, and carbon black).

EXAMPLES

Hereinafter, an example of the present invention is described in more detail by way of examples and comparative examples; however, the present invention is not limited to the following description.

Tables 4 to 6 show compositions of flaky particles used for producing bright pigments of Examples 1 to 23 and Comparative Examples 1 to 7.

TABLE 4

Composition of flaky glass particles

|  | Examples 2, 5, 7, 10, 13, 20 | Examples 1, 4, 6, 9, 12, 15 to 19 | Examples 3, 8, 11, 14, 23 C glass | Comparative Examples 1, 2, 3, 4, 5 |
|---|---|---|---|---|
| $SiO_2$ | 65.4 | 64 | 66.8 | 61.8 |
| $Al_2O_3$ | 11 | 11 | 4.7 | 11.2 |
| CaO | 15 | 10.3 | 6.6 | 21.8 |
| MgO | 2.3 | 2.9 | 2.6 | 3 |
| $B_2O_3$ | 0 | 0 | 4.1 | — |
| $Na_2O$ | 3.8 | 8.9 | 10.3 | 0.4 |
| $K_2O$ | 0.5 | 0.8 | 0.8 | 0.3 |
| $Li_2O$ | 1.9 | 2 | 0.6 | — |
| ZnO | 0.1 | 0.1 | 3.6 | — |
| $TiO_2$ | — | — | — | 1.6 |
| $FeO/Fe_2O_3$ | — | — | 0 | — |

(Unit: % by mass)

TABLE 5

Composition of flaky alumina particles

|  | Example 21 | Comparative Example 6 |
|---|---|---|
| $Al_2O_3$ | 92.8 | 78.5 |
| $Na_2O$ | 4.2 | 1.3 |
| $K_2O$ | 2 | 17.4 |
| $TiO_2$ | — | 1 |
| $P_2O_5$ | 1 | 1.8 |

(Unit: % by mass)

TABLE 6

Composition of synthetic mica particles

|  | Comparative Example 7 Fluorine gold mica $KMg_3(AlSi_3O_{10})F_2$ | Example 22 Sodium tetrasilicon mica $NaMg_{2.5}(Si_4O_{10})F_2$ |
|---|---|---|
| $SiO_2$ | 43 | 60.8 |
| $Al_2O_3$ | 10.5 | — |
| MgO | 29.1 | 24.6 |
| $Na_2O$ | 0.9 | 4.1 |
| $K_2O$ | 7.5 | — |
| F | 9 | 10.5 |

(Unit: % by mass)

Example 1

A bright pigment of Example 1 is flaky glass particles (refractive index: 1.53, average thickness: 1.3 μm, and particle diameter D50: about 85 μm) each covered with rutile titanium dioxide ($TiO_2$).

First, a tapered cup attached to a variable-speed electric motor was rotated at a predetermined speed by an apparatus shown in FIG. 2 for producing flaky glass particles through use of a flow of molten glass, and molten glass was poured into the cup from above. The molten glass in the cup was sent outside beyond a rim due to centrifugal force and crushed into small flaky glass while being kept in a plate shape by an airflow. The flaky glass thus obtained was collected in a chamber. Then, the flaky glass was sent to a cyclone collection/filtration section and further cooled to be solidified. The flaky glass thus obtained was pulverized through use of a jet mill type pulverizer with the intention that the flaky glass had an average particle diameter of 100 μm. Thus, flaky glass particles having a particle diameter D50 of 100.7 μm were produced. Factors for determining a thickness distribution are the stability of a flow rate of molten glass, the distance between plates 24, 25, the speed of an airflow between the plates 24, 25, and the like.

The flaky glass particles were classified. Using a sieve with a mesh opening of 115 μm, and arranging a receiving tray below the sieve, the flaky glass particles were sieved for a predetermined period of time so that coarse particles were removed. The flaky glass particles collected by the receiving tray each were obtained as a base material (a flaky particle) of the bright pigment of Example 1. The particle size distribution, refractive index, and thickness of the flaky glass particles thus obtained were measured. The particle diameter (D50) was 84.3 μm; the refractive index was 1.53; and the average thickness was 1.3 μm. The zeta potential of the flaky glass particles in hydrochloric acid aqueous solution (pH=2.0) was −19 mV.

Next, the classified flaky glass particles were treated with tin oxide (catalytic nucleus), and thereafter were covered with titanium dioxide. The catalytic nucleus refers to a substance to be a catalyst for deposition of a covering film of a hydrate of titanium dioxide. Specifically, the following was performed.

First, 3 L of ion-exchanged water at room temperature was adjusted to pH 1.6 with hydrochloric acid while stirring, and 300 g of flaky glass was added to the resultant to obtain a slurry. To this slurry, a tin solution, in which 2 g of stannic chloride has been dissolved in 30 mL of hydrochloric acid aqueous solution of pH 2 in advance, were added quantitatively at a rate of 1.5 ml per minute. Then, while this state was kept for 20 minutes, the flaky glass particles were subjected to a surface treatment with tin oxide.

Then, the resultant slurry was heated to 75° C. while adjusting the pH to 1.0 with 35% by mass of hydrochloric acid. While stirring, a titanium tetrachloride aqueous solution (containing 16.5% by mass of titanium) was added quantitatively at a rate of 2.0 mL/minute to the obtained slurry, and caustic soda obtained by dissolving sodium hydroxide in an amount of 10% by mass was added so as to keep the pH of the slurry to be 1.0. Caustic soda continued to be added until a product having glittering appearance and a silver pearl tone was obtained.

After a product with the target color tone was obtained, the product was collected by filtration under reduced pressure, washed with pure water, dried at 150° C., and baked at 600° C.

Thus, the bright pigment of Example 1, in which flaky glass particles were covered with a layer (metal oxide layer) substantially made of titanium dioxide, was obtained through the above-mentioned method.

Example 2

A bright pigment of Example 2 was produced in the same way as in Example 1 except that the composition of flaky glass particles was different. The bright pigment of Example 2 is flaky glass particles each covered with a layer (metal oxide layer) substantially made of rutile titanium dioxide ($TiO_2$).

Example 3

A bright pigment of Example 3 was produced in the same way as in Example 1 except that the composition of flaky glass particles was different. The bright pigment of Example 3 is flaky glass particles each covered with a layer (metal oxide layer) substantially made of rutile titanium dioxide ($TiO_2$).

Example 4

A bright pigment of Example 4 was produced in the same way as in Example 1 except for setting the average thickness of flaky glass particles to 5.0 μm and setting the particle diameter D50 to about 105 μm. The bright pigment of Example 4 is flaky glass particles each covered with a layer (metal oxide layer) substantially made of rutile titanium dioxide ($TiO_2$).

Example 5

A bright pigment of Example 5 was produced in the same way as in Example 1 except for setting the composition of flaky glass particles to be the same as that of Example 2, setting the average thickness of flaky glass particles to 5.0 μm and setting the particle diameter D50 to about 105 μm. The bright pigment of Example 5 is flaky glass particles each covered with a layer (metal oxide layer) substantially made of rutile titanium dioxide ($TiO_2$).

Example 6

A bright pigment of Example 6 was produced in the same way as in Example 1 except for setting the average thickness of flaky glass particles to 1.3 μm, setting the particle diameter D50 to about 85 μm, and using reduced titanium oxide for the metal oxide layer. The bright pigment of Example 6 is flaky glass particles each covered with a layer (metal oxide layer) substantially made of reduced titanium oxide. The layer (metal oxide layer) substantially made of reduced titanium oxide ($TiO_{1.7}$) was produced as follows.

Flaky glass particles covered with a titanium dioxide layer produced by the same method as that of Example 1 were put in a platinum tray and subjected to a heat treatment at a temperature of 600° C. for 10 hours while ammonia gas was caused to flow in a tubular furnace. Thus, titanium dioxide was reduced to black lower-order titanium oxide ($TiO_x$, x=1.7), with the result that flaky glass particles covered with a lower-order titanium oxide (reduced titanium oxide) layer were obtained.

Example 7

A bright pigment of Example 7 was produced in the same way as in Example 6 except for setting the composition of flaky glass particles to be the same as that of Example 2. The bright pigment of Example 7 is flaky glass particles each covered with a layer (metal oxide layer) substantially made of reduced titanium oxide ($TiO_{1.7}$)

Example 8

A bright pigment of Example 8 was produced in the same way as in Example 6 except for setting the composition of flaky glass particles to be the same as that of Example 3. The bright pigment of Example 8 is flaky glass particles each covered with a layer (metal oxide layer) substantially made of reduced titanium oxide ($TiO_{1.7}$).

Example 9

A bright pigment of Example 9 is flaky glass particles each covered with a layer (metal oxide layer) substantially made of iron oxide. The average thickness of the flaky glass particles used for producing the bright pigment of Example 9 was set to 1.3 μm and the particle diameter D50 thereof was set to about 85 μm. The composition of the flaky glass particles was set to be the same as that of Example 1. The layer (metal oxide layer) substantially made of iron oxide ($Fe_2O_3$) was produced as follows.

First, 100 g of flaky glass particles were added to and dispersed in 1 L of purified water and increased in temperature to 75° C. and held in a constant temperature bath. A slurry thus obtained was adjusted to about pH 3.2 with diluted hydrochloric acid. After that, a 10% iron chloride (III) solution was added to the slurry. In this case, the pH of the slurry was kept at about 3.2 with a diluted sodium hydroxide solution. Thus, the surface of each flaky glass particle was covered with a hydrate of $Fe_2O_3$. The 10% iron chloride (III) solution continued to be added to the resultant slurry until red interference color was obtained. After the completion of the addition of the 10% iron chloride (III) solution, a suspension of the flaky glass particles was filtered. A collected residue was dried (180° C.) and baked at 600° C. for 2 hours, with the result that a bright pigment in which flaky glass particles were each covered with a layer (metal oxide layer) substantially made of iron oxide ($Fe_2O_3$) was obtained.

Example 10

A bright pigment of Example 10 was produced in the same way as in Example 9 except for setting the composition of flaky glass particles to be the same as that of Example 2. The bright pigment of Example 10 is flaky glass particles each covered with a layer (metal oxide layer) substantially made of iron oxide ($Fe_2O_3$).

Example 11

A bright pigment of Example 11 was produced in the same way as in Example 9 except for setting the composition of flaky glass particles to be the same as that of Example 3. The bright pigment of Example 11 is flaky glass particles each covered with a layer (metal oxide layer) substantially made of iron oxide ($Fe_2O_3$).

Example 12

A bright pigment of Example 12 is flaky glass particles each covered with a layer (metal oxide layer) substantially made of reduced iron oxide ($Fe_3O_4$). The average thickness of the flaky glass particles used for producing the bright pigment of Example 12 was set to 1.3 μm, the particle diameter D50 thereof was set to about 85 μm, and the composition thereof was set to be the same as that of Example 1. The layer (metal oxide layer) substantially made of reduced iron oxide ($Fe_3O_4$) was produced as follows.

Flaky glass particles covered with a layer (metal oxide layer) substantially made of iron oxide ($Fe_2O_3$) produced in the same way as in Example 9 were put in a platinum tray and subjected to a heat treatment at a reducing temperature of 500° C. for 2 hours while gas containing 10% hydrogen and 90% nitrogen was caused to flow in a tubular furnace. Thus, $Fe_3O_4$ was reduced to black $Fe_3O_4$.

Example 13

A bright pigment of Example 13 was produced in the same way as in Example 12 except for setting the composition of flaky glass particles to be the same as that of Example 2. The bright pigment of Example 13 is flaky glass particles each covered with a layer (metal oxide layer) substantially made of reduced iron oxide ($Fe_3O_4$).

Example 14

A bright pigment of Example 14 was produced in the same way as in Example 12 except for setting the composition of flaky glass particles to be the same as that of Example 3. The bright pigment of Example 14 is flaky glass particles each covered with a layer (metal oxide layer) substantially made of reduced iron oxide ($Fe_3O_4$).

Example 15

A bright pigment of Example 15 is flaky glass particles (refractive index: 1.53, average thickness: 0.45 μm, particle diameter (D50): 24.1 μm) each covered with rutile titanium dioxide.

First, a tapered cup attached to a variable-speed electric motor was rotated at predetermined speed by an apparatus shown in FIG. 2 for producing flaky glass particles through use of a flow of molten glass, and molten glass was poured into the cup from above. The molten glass in the cup was sent outside beyond a rim due to centrifugal force and crushed into small flaky glass while being kept in a plate shape by an airflow. The flaky glass thus obtained was collected in a chamber. Then, the flaky glass was sent to a cyclone collection/filtration section and further cooled to be solidified. The flaky glass thus obtained was pulverized through use of a jet mill type pulverizer with the intention that the flaky glass had an average particle diameter of 40 μm. Thus, flaky glass particles having a particle diameter D50 of 40.1 μm were produced. Factors for determining a thickness distribution are the stability of a flow rate of molten glass, the distance between plates 24, 25, the speed of an airflow between the plates 24, 25, and the like.

The flaky glass particles were classified. Using a sieve with a mesh opening of 45 μm, and arranging a receiving tray below the sieve, the flaky glass particles were sieved for a predetermined period of time so that coarse particles were removed. The flaky glass collected by the receiving tray each were obtained as a base material (a flaky particle) of the bright pigment of the present example. The particle size distribution and thickness of the flaky glass particles thus obtained were measured. The particle diameter (D50) was 24.1 μm; the refractive index was 1.53; and the average thickness was 0.45 μm. The zeta potential of the flaky glass in hydrochloric acid aqueous solution (pH=2.0) was −19 mV.

Next, the classified flaky glass particles were treated with tin oxide (catalytic nucleus), and thereafter were covered with titanium dioxide. The catalytic nucleus refers to a substance to be a catalyst for deposition of a hydrate of titanium dioxide. Specifically, the following was performed.

First, 3 L of ion-exchanged water at room temperature was adjusted to pH 1.6 with hydrochloric acid while stirring, and 300 g of flaky glass was added to the resultant to obtain a slurry. To this slurry, a tin solution, in which 2 g of stannic chloride has been dissolved in 30 mL of hydrochloric acid aqueous solution of pH 2 in advance, were added quantitatively at a rate of 1.5 ml per minute. Then, while this state was kept for 20 minutes, the flaky glass particles were subjected to a surface treatment with tin oxide.

Then, the resultant slurry was heated to 75° C. while adjusting the pH to 1.0 with 35% by mass of hydrochloric acid. While stirring, a titanium tetrachloride aqueous solution (containing 16.5% by mass of titanium) was added quantitatively at a rate of 2.0 mL/minute to the obtained slurry, and caustic soda obtained by dissolving sodium hydroxide in an amount of 10% by mass was added so as to keep the pH of the slurry to be 1.0. Caustic soda continued to be added until a product having glittering appearance and a silver pearl tone was obtained.

After a product with the target color tone was obtained, the product was collected by filtration under reduced pressure, washed with pure water, dried at 150° C., and baked at 600° C.

Thus, the bright pigment of Example 15, in which flaky glass particles were covered with a layer (metal oxide layer) substantially made of titanium dioxide, was obtained through the above-mentioned method.

The particle diameter (D50) of the bright pigment of Example 15 thus obtained was 24.5 μm, the specific surface area thereof was 1.7 $m^2/g$, and the thickness variation coefficient of a titanium dioxide layer was 7.4%. The obtained bright pigment was dissolved in hydrofluoric acid and subjected to ICP analysis. Consequently, it was found that the content of $Na_2O$ contained in the flaky particles obtained by removing the metal oxide layer from the bright pigment was 8.7% by mass.

Example 16

A bright pigment of Example 16 is flaky glass particles (refractive index: 1.53, average thickness: 0.35 μm, particle diameter (D50): 24.3 μm) each covered with rutile titanium dioxide.

First, flaky glass was obtained in the same way as in Example 15 except for producing the flaky glass so as to adjust the average thickness to 0.35 μm through use of the apparatus shown in FIG. 2. The flaky glass thus obtained was pulverized through use of a jet mill type pulverizer with the intention that the flaky glass had an average particle diameter of 40 μm. Thus, flaky glass particles having a particle diameter D50 of 40.9 μm were produced.

The flaky glass particles were classified in the same way as in Example 15, and the flaky glass particles collected in a receiving tray were obtained as a base material (flaky particles) of the bright pigment of the present example. The particle diameter (D50) of the flaky glass particles thus obtained was 24.3 μm, the refractive index thereof was 1.53, and the average thickness thereof was 0.35 μm. The zeta potential of the flaky glass particles in hydrochloric acid aqueous solution (pH=2.0) was −19 mV.

After that, in the same way as in Example 15, flaky glass particles each covered with a titanium dioxide layer (metal oxide layer) having glittering appearance and a silver pearl tone were obtained as a bright pigment of Example 16. The particle diameter (D50) of the bright pigment of Example 16 thus obtained was 24.6 μm, the specific surface area thereof was 1.7 $m^2/g$, and the thickness variation coefficient of a titanium dioxide layer was 7.4%. The obtained bright pigment was dissolved in hydrofluoric acid and subjected to ICP analysis. Consequently, it was found that the content of $Na_2O$ contained in the flaky particles obtained by removing the metal oxide layer from the bright pigment was 8.7% by mass.

Example 17

A bright pigment of Example 17 is flaky glass particles (refractive index: 1.53, average thickness: 0.55 μm, particle diameter (D50): 24.4 μm) each covered with rutile titanium dioxide.

First, flaky glass was obtained in the same way as in Example 15 except for producing the flaky glass so as to adjust the average thickness to 0.55 μm through use of the apparatus shown in FIG. 2. The flaky glass thus obtained was pulverized through use of a jet mill type pulverizer with the intention that the flaky glass had an average particle diameter of 40 μm. Thus, flaky glass particles having a particle diameter D50 of 40.5 μm were produced.

The flaky glass particles were classified in the same way as in Example 15, and the flaky glass particles collected in a receiving tray were obtained as a base material (flaky particles) of the bright pigment of the present example. The particle diameter (D50) of the flaky glass particles thus obtained was 24.4 μm, the refractive index thereof was 1.53, and the average thickness thereof was 0.55 μm. The zeta potential of the flaky glass particles in hydrochloric acid aqueous solution (pH=2.0) was −19 mV.

After that, flaky glass particles each covered with a titanium dioxide layer (metal oxide layer) having glittering appearance and a silver pearl tone were obtained as a bright pigment of Example 17 in the same way as in Example 15.

The particle diameter (D50) of the bright pigment of Example 17 thus obtained was 24.6 μm, the specific surface area thereof was 1.7 m$^2$/g, and the thickness variation coefficient of a titanium dioxide layer was 7.4%. The obtained bright pigment was dissolved in hydrofluoric acid and subjected to ICP analysis. Consequently, it was found that the content of $Na_2O$ contained in the flaky particles obtained by removing the metal oxide layer from the bright pigment was 8.7% by mass.

Example 18

A bright pigment of Example 18 is flaky glass particles (refractive index: 1.53, average thickness: 0.45 μm, particle diameter (D50): 21.4 μm) each covered with rutile titanium dioxide.

First, flaky glass was obtained by the same method as that of Example 15 except for producing the flaky glass so as to adjust the average thickness to 0.45 μm through use of the apparatus shown in FIG. 2. The flaky glass thus obtained was pulverized through use of a jet mill type pulverizer with the intention that the flaky glass had an average particle diameter of 35 μm. Thus, flaky glass particles having a particle diameter D50 of 35.8 μm were produced.

The flaky glass particles were classified in the same way as in Example 15, and the flaky glass collected in a receiving tray was obtained as a base material (flaky particles) of the bright pigment of the present example. It should be noted that the mesh size of a sieve was 38 μm. The particle diameter (D50) of the flaky glass particles thus obtained was 21.4 μm, the refractive index thereof was 1.53, and the average thickness thereof was 0.45 μm. The zeta potential of the flaky glass particles in hydrochloric acid aqueous solution (pH=2.0) was −19 mV.

After that, flaky glass particles each covered with a titanium dioxide covering film (metal oxide layer) having glittering appearance and a silver pearl tone were obtained as a bright pigment of Example 18 in the same way as in Example 15.

The particle diameter (D50) of the bright pigment of Example 18 thus obtained was 21.8 μm, the specific surface area thereof was 1.7 m$^2$/g, and the thickness variation coefficient of a titanium dioxide layer was 7.4%. The obtained bright pigment was dissolved in hydrofluoric acid and subjected to ICP analysis. Consequently, it was found that the content of $Na_2O$ contained in the flaky particles obtained by removing the metal oxide layer from the bright pigment was 8.7% by mass.

Example 19

A bright pigment of Example 19 is flaky glass particles (refractive index: 1.53, average thickness: 0.45 μm, particle diameter (D50): 28.4 μm) each covered with rutile titanium dioxide.

First, flaky glass was obtained by the same method as that of Example 15 except for producing the flaky glass so as to adjust the average thickness to 0.45 μm through use of the apparatus shown in FIG. 2. The flaky glass thus obtained was pulverized through use of a jet mill type pulverizer with the intention that the flaky glass had an average particle diameter of 45 μm. Thus, flaky glass particles having a particle diameter D50 of 46.8 μm were produced.

The flaky glass particles were classified in the same way as in Example 15, and the flaky glass particles collected in a receiving tray were obtained as a base material (flaky particles) of the bright pigment of the present example. The particle size distribution, refractive index, and thickness of the flaky glass particles thus obtained were measured to find that flaky glass having a particle diameter (D50) of 28.4 μm, a refractive index of 1.53, and an average thickness of 0.45 μm was obtained. The zeta potential of the flaky glass particles in hydrochloric acid aqueous solution (pH=2.0) was −19 mV.

After that, flaky glass particles each covered with a titanium dioxide covering film (metal oxide layer) having glittering appearance and a silver pearl tone were obtained as a bright pigment of Example 19 in the same way as in Example 15.

The particle diameter (D50) of the bright pigment of Example 19 thus obtained was 28.9 μm, the specific surface area thereof was 1.7 m$^2$/g, and the thickness variation coefficient of a titanium dioxide layer was 7.4%. The obtained bright pigment was dissolved in hydrofluoric acid and subjected to ICP analysis. Consequently, it was found that the content of $Na_2O$ contained in the flaky particles obtained by removing the metal oxide layer from the bright pigment was 8.7% by mass.

Example 20

A bright pigment of Example 20 is flaky glass particles (refractive index: 1.54, average thickness: 0.45 μm, particle diameter (D50): 25.2 μm) each covered with rutile titanium dioxide.

First, flaky glass was obtained by the same method as that of Example 15 except for producing the flaky glass so as to adjust the average thickness to 0.45 μm through use of the apparatus shown in FIG. 2. The flaky glass thus obtained was pulverized through use of a jet mill type pulverizer with the intention that the flaky glass had an average particle diameter of 40 μm. Thus, flaky glass particles having a particle diameter D50 of 41.8 μm were produced.

The flaky glass particles were classified in the same way as in Example 15, and the flaky glass particles collected in a receiving tray were obtained as a base material (flaky particles) of the bright pigment of the present example. The particle diameter (D50) of the flaky glass particles thus obtained was 25.2 μm, the refractive index thereof was 1.54, and the average thickness thereof was 0.45 μm. The zeta potential of the flaky glass particles in hydrochloric acid aqueous solution (pH=2.0) was −11 mV.

After that, flaky glass particles each covered with a titanium dioxide covering film (metal oxide layer) having glittering appearance and a silver pearl tone were obtained as a bright pigment of Example 20 in the same way as in Example 15.

The particle diameter (D50) of the bright pigment of Example 20 thus obtained was 25.4 µm, the specific surface area thereof was 2.8 m$^2$/g, and the thickness variation coefficient of a titanium dioxide layer was 18.3%. The obtained bright pigment was dissolved in hydrofluoric acid and subjected to ICP analysis. Consequently, it was found that the content of $Na_2O$ contained in the flaky particles obtained by removing the metal oxide layer from the bright pigment was 3.7% by mass.

Example 21

A bright pigment of Example 21 is flaky alumina particles (refractive index: 1.76, average thickness: 0.35 µm, particle diameter (D50): 19.9 µm) each covered with rutile titanium dioxide.

223.8 g of aluminium sulfate octadecahydrate, 114.5 g of sodium sulfate (anhydride), and 93.7 g of potassium sulfate were added to 450 ml of desalted water and dissolved therein while being heated to about 75° C. After the completion of dissolution, 2.0 g of a titanyl sulfate solution (concentration: 34.4%) were added to the resultant solution to prepare a mixed aqueous solution (a). Separately, 0.9 g of trisodium phosphate dodecahydrate and 107.9 g of sodium carbonate were dissolved in 250 ml of desalted water to prepare a mixed aqueous solution (b). The mixed aqueous solutions (a) and (b) were added to 200 ml of desalted water while stirring at a predetermined speed over about 15 minutes so that the aqueous solutions (a) and (b) became almost equivalent to each other, and the mixture was further stirred for 15 minutes. The solution thus obtained was dried by evaporation and then subjected to a heat treatment at 1,200° C. for 5 hours. Water was added to the treated material thus obtained so as to dissolve a free sulfate in water. Then, an insoluble solid was separated by filtration, washed with water, and dried to obtain flaky alumina particles.

The flaky alumina particles thus obtained had a particle diameter (D50) of 19.9 µm, a refractive index of 1.76, and an average thickness of 0.35 µm. The zeta potential of the flaky alumina particles in hydrochloric acid aqueous solution (pH=2.0) was −13 mV.

Then, flaky alumina particles covered with a titanium dioxide covering film (metal oxide layer) having glittering appearance and a silver pearl tone were obtained as the bright pigment of Example 21 in the same way as in Example 15.

The particle diameter (D50) of the obtained bright pigment of Example 21 was 20.5 µm, the specific surface area thereof was 2.3 m$^2$/g, and the thickness variation coefficient of a titanium dioxide layer was 18.2%. The obtained bright pigment was dissolved in hydrofluoric acid and subjected to ICP analysis. As a result, the content of $Na_2O$ contained in flaky particles obtained by removing the metal oxide layer from the bright pigment was 3.9% by mass.

Example 22

A bright pigment of Example 22 is synthetic mica particles (commercially available sodium tetrasilicon mica $NaMg_{2.5}(Si_4O_{10})F_2$, refractive index: 1.58, average thickness: 0.35 µm) each covered with rutile titanium dioxide.

The commercially available synthetic mica particles were classified in the same way as in Example 15, and the flaky glass particles collected by the receiving tray were obtained as a base material (a flaky particle) of the bright pigment of the present example. The synthetic mica particles thus obtained had an average particle diameter (D50) of 20.2 µm, a refractive index of 1.58, and an average thickness of 0.35 µm. The zeta potential of the synthetic mica particles in hydrochloric acid aqueous solution (pH=2.0) was −13 mV.

Then, synthetic mica particles covered with a titanium dioxide covering film (metal oxide layer) having glittering appearance and a silver pearl tone were obtained as the bright pigment of Example 22 in the same way as in Example 15.

The particle diameter (D50) of the obtained bright pigment of Example 22 was 20.4 µm, the specific surface area thereof was 2.5 m$^2$/g, and the thickness variation coefficient of a titanium dioxide layer was 18.3%. The obtained bright pigment was dissolved in hydrofluoric acid and subjected to ICP analysis. As a result, the content of $Na_2O$ contained in flaky particles obtained by removing the metal oxide layer from the bright pigment was 3.9% by mass.

Example 23

A bright pigment of Example 23 is flaky glass particles (refractive index: 1.52, average thickness: 0.45 µm, particle diameter (D50): 24.5 µm) each covered with rutile titanium dioxide.

First, flaky glass was obtained by the same method as that of Example 15 except for producing the flaky glass so as to adjust the average thickness to 0.45 µm through use of the apparatus shown in FIG. 2. The flaky glass thus obtained was pulverized through use of a jet mill type pulverizer with the intention that the flaky glass had an average particle diameter of 40 µm. Thus, flaky glass particles having a particle diameter D50 of 41.8 µm were produced.

The flaky glass particles were classified in the same way as in Example 15, and the flaky glass particles collected in a receiving tray were obtained as a base material (flaky particles) of the bright pigment of the present example. The particle diameter (D50) of the flaky glass particles thus obtained was 24.5 µm, the refractive index thereof was 1.52, and the average thickness thereof was 0.45 µm. The zeta potential of the flaky glass particles in hydrochloric acid aqueous solution (pH=2.0) was −23 mV.

After that, flaky glass particles each covered with a titanium dioxide covering film (metal oxide layer) having glittering appearance and a silver pearl tone were obtained as a bright pigment of Example 23 in the same way as in Example 15.

The particle diameter (D50) of the bright pigment of Example 23 thus obtained was 24.7 µm, the specific surface area thereof was 1.7 m$^2$/g, and the thickness variation coefficient of a titanium dioxide layer was 7.4%. The obtained bright pigment was dissolved in hydrofluoric acid and subjected to ICP analysis. Consequently, it was found that the content of $Na_2O$ contained in the flaky particles obtained by removing the metal oxide layer from the bright pigment was 10.2% by mass.

Comparative Example 1

A bright pigment of Comparative Example 1 was produced in the same way as in Example 1 except that the composition of flaky glass particles was different. The bright pigment of Comparative Example 1 is flaky glass particles each covered with a layer (metal oxide layer) substantially made of titanium dioxide ($TiO_2$).

Comparative Example 2

A bright pigment of Comparative Example 2 was produced in the same way as in Example 6 except for setting the composition of flaky glass particles to be the same as that of Comparative Example 1. The bright pigment of Comparative Example 2 is flaky glass particles covered with a layer (metal oxide layer) substantially made of reduced titanium oxide ($TiO_{1.7}$).

Comparative Example 3

A bright pigment of Comparative Example 3 was produced in the same way as in Example 9 except for setting the composition of flay glass particles to be the same as that of Comparative Example 1. The bright pigment of Comparative Example 3 is flaky glass particles each covered with a layer (metal oxide layer) substantially made of iron oxide ($Fe_2O_3$).

Comparative Example 4

A bright pigment of Comparative Example 4 was produced in the same way as in Example 12 except for setting the composition of the flaky glass particles to be the same as that of Comparative Example 1. The bright pigment of Comparative Example 4 is flaky glass particles each covered with a layer (metal oxide layer) substantially made of reduced iron oxide ($Fe_3O_4$).

Comparative Example 5

A bright pigment of Comparative Example 5 is flaky glass particles (refractive index: 1.57, average thickness: 0.45 μm, particle diameter (D50): 24.2 μm) each covered with rutile titanium dioxide.

First, flaky glass was obtained by the same method as that of Example 15 except for producing the flaky glass so as to adjust the average thickness to 0.45 μm through use of the apparatus shown in FIG. 2. The flaky glass thus obtained was pulverized through use of a jet mill type pulverizer with the intention that the flaky glass had an average particle diameter of 40 μm. Thus, flaky glass particles having a particle diameter D50 of 41.3 μm were produced.

The flaky glass particles were classified in the same way as in Example 15, and the flaky glass particles collected in a receiving tray were obtained as a base material (flaky particles) of the bright pigment of the present example. The particle diameter (D50) of the flaky glass particles thus obtained was 24.2 μm, the refractive index thereof was 1.57, and the average thickness thereof was 0.45 μm. The zeta potential of the flaky glass particles in hydrochloric acid aqueous solution (pH=2.0) was −4 mV.

After that, flaky glass particles each covered with a titanium dioxide covering film (metal oxide layer) having glittering appearance and a silver pearl tone were obtained as a bright pigment of Comparative Example 5 in the same way as in Example 15.

The particle diameter (D50) of the bright pigment of Comparative Example 5 thus obtained was 24.4 μm, the specific surface area thereof was 8.7 $m^2$/g, and the thickness variation coefficient of a titanium dioxide layer was 24.0%. The obtained bright pigment was dissolved in hydrofluoric acid and subjected to ICP analysis. Consequently, it was found that the content of $Na_2O$ contained in the flaky particles obtained by removing the metal oxide layer from the bright pigment was 0.4% by mass.

Comparative Example 6

A bright pigment of Comparative Example 6 is flaky alumina particles (refractive index: 1.76, average thickness: 0.30 μm, and particle diameter (D50): 19.7 μm) each covered with rutile titanium dioxide.

First, aluminum hydroxide serving as a starting material was pulverized through use of a ball mill or the like in advance, and the particle size thereof was adjusted to 3.0 μm. The particles thus obtained were mixed with water to prepare 50% by weight of a slurry. Then, ammonium phosphate was added to the slurry as phosphate ions in an amount of $5.0 \times 10^{-3}$ mol with respect to aluminum hydroxide and thoroughly dissolved in the slurry by mixing.

A pressure vessel was filled with the resultant material. The material was raised in temperature to 600° C. at a temperature rise speed of 0.3° C./min by an electric furnace and kept at a pressure of 150 atmospheres for 3 hours. The vessel was cooled, and the product thus obtained was washed with pure water. Then the product was subjected to filtration sufficiently and dried in a drier at 100° C. for 12 hours to obtain white particle powder (flaky particles). The flaky alumina particles thus obtained had a particle diameter (D50) of 19.7 μm, a refractive index of 1.76, and an average thickness of 0.30 μm. The zeta potential of the flaky alumina particles in hydrochloric acid aqueous solution (pH=2.0) was −5 mV.

Then, flaky alumina particles covered with a titanium dioxide covering film (metal oxide layer) having glittering appearance and a silver pearl tone were obtained as the bright pigment of Comparative Example 6 in the same way as in Example 15.

The particle diameter (D50) of the obtained bright pigment of Comparative Example 6 was 20.3 μm, the specific surface area thereof was 9.3 $m^2$/g, and the thickness variation coefficient of a titanium dioxide layer was 24.2%. The obtained bright pigment was dissolved in hydrofluoric acid and subjected to ICP analysis. As a result, the content of $Na_2O$ contained in flaky particles obtained by removing the metal oxide layer from the bright pigment was 0.9% by mass.

Comparative Example 7

A bright pigment of Comparative Example 7 is synthetic mica particles (commercially available fluorine gold mica $KMg_3(AlSi_3O_{10})F_2$, refractive index: 1.58, average thickness: 0.25 μm) covered with rutile titanium dioxide.

The commercially available synthetic mica particles were classified in the same way as in Example 1, and the flaky glass collected by the receiving tray was obtained as a base material (a flaky particle) of the bright pigment of Comparative Example 7. It should be noted that a mesh size of a sieve was set to 45 μm. The flaky synthetic mica particles thus obtained had a particle diameter (D50) of 19.2 μm, a refractive index of 1.58, and an average thickness of 0.25 μm. The zeta potential of the flaky synthetic mica in hydrochloric acid aqueous solution (pH=2.0) was −7 mV.

Then, flaky synthetic mica particles covered with a titanium dioxide covering film (metal oxide layer) having glittering appearance and a silver pearl tone were obtained as the bright pigment of Comparative Example 7 in the same way as in Example 15.

The particle diameter (D50) of the obtained bright pigment of Comparative Example 7 was 20.1 µm, the specific surface area thereof was 10.5 m²/g, and the thickness variation coefficient of a titanium dioxide layer was 25.3%. The obtained bright pigment was dissolved in hydrofluoric acid and subjected to ICP analysis. As a result, the content of Na$_2$O contained in flaky particles obtained by removing the metal oxide layer from the bright pigment was 0.8% by mass.

The particle diameter (D50), refractive index 1.53, average thickness, zeta potential, and content of Na$_2$O of the flaky particles, and the particle diameter (D50), specific surface area, and thickness variation coefficient of a metal oxide layer of the bright pigment, measured for the obtained bright pigments of Examples 1 to 23 and Comparative Examples 1 to 7, were obtained by the following methods and shown in Tables 7 to 9. Further, the obtained bright pigments were dissolved in hydrofluoric acid and subjected to ICP analysis, whereby the content of Na$_2$O contained in flaky particles obtained by removing the metal oxide layer from the bright pigment was measured and shown in Tables 7 to 9.

TABLE 7

|  | Example 1 | Example 2 | Example 3 | Example 4 | Example 5 | Example 6 | Example 7 | Example 8 | Example 9 | Example 10 |
|---|---|---|---|---|---|---|---|---|---|---|
| Kind of flaky particles | Glass | Glass | Glass | Glass | Glass | Glass | Glass | Glass | Glass | Glass |
| Refractive index of flaky particles | 1.53 | 1.54 | 1.52 | 1.53 | 1.54 | 1.53 | 1.54 | 1.52 | 1.53 | 1.54 |
| Average thickness of flaky particles (µm) | 1.3 | 1.3 | 1.3 | 5.0 | 5.0 | 1.3 | 1.3 | 1.3 | 1.3 | 1.3 |
| Particle diameter (D50) of flaky particles (µm) | 84.3 | 84.5 | 84.6 | 107.3 | 107.3 | 84.5 | 84.6 | 84.5 | 84.5 | 84.3 |
| Zeta potential of flaky particles (mV) | −19 | −19 | −23 | −18 | −18 | −19 | −19 | −23 | −19 | −19 |
| Content of Na$_2$O (% by mass)$^{Note1)}$ | 8.7 | 3.7 | 10.2 | 8.7 | 3.7 | 8.7 | 3.7 | 10.2 | 8.7 | 3.7 |
| Kind of metal oxide | Titanium dioxide | Titanium dioxide | Titanium dioxide | Titanium dioxide | Titanium dioxide | Reduced titanium oxide | Reduced titanium oxide | Reduced titanium oxide | Iron oxide | Iron oxide |
| Particle diameter (D50) of bright pigment (µm) | 84.5 | 84.4 | 84.3 | 104.8 | 105.4 | 84.3 | 84.5 | 84.3 | 84.6 | 84.3 |
| Specific surface area of bright pigment (m²/g) | 1.6 | 2.4 | 2.1 | 1.4 | 2.2 | 1.6 | 1.6 | 2.1 | 2.2 | 2.9 |
| Thickness variation coefficient of metal oxide layer (%) | 7.4 | 17.4 | 17.4 | 7.4 | 17.0 | 7.4 | 17.3 | 17.4 | 17.0 | 19.4 |
| Luminosity L* (−15°) | 143.3 | 143.8 | 143.5 | 141.6 | 142.1 | 130.3 | 130.6 | 130.4 | 97.6 | 97.1 |
| Chromaticness (C*) | 5.67 | 5.59 | 5.61 | 5.39 | 5.30 | 4.59 | 4.53 | 4.57 | 35.00 | 35.60 |

|  | Example 11 | Example 12 | Example 13 | Example 14 | Comparative Example 1 | Comparative Example 2 | Comparative Example 3 | Comparative Example 4 |
|---|---|---|---|---|---|---|---|---|
| Kind of flaky particles | Glass | Glass | Glass | Glass | Glass | Glass | Glass | Glass |
| Refractive index of flaky particles | 1.52 | 1.53 | 1.54 | 1.52 | 1.57 | 1.57 | 1.57 | 1.57 |
| Average thickness of flaky particles (µm) | 1.3 | 1.3 | 1.3 | 1.3 | 1.3 | 1.3 | 1.3 | 1.3 |
| Particle diameter (D50) of flaky particles (µm) | 84.6 | 84.3 | 84.5 | 84.5 | 84.5 | 84.5 | 84.5 | 84.6 |
| Zeta potential of flaky particles (mV) | −23 | −19 | −19 | −23 | −4 | −4 | −4 | −4 |
| Content of Na$_2$O (% by mass) $^{Note1)}$ | 10.2 | 8.7 | 3.7 | 10.2 | 0.4 | 0.4 | 0.4 | 0.4 |
| Kind of metal oxide | Iron oxide | Reduced iron oxide | Reduced iron oxide | Reduced iron oxide | Titanium dioxide | Reduced titanium oxide | Iron oxide | Reduced iron oxide |
| Particle diameter (D50) of bright pigment (µm) | 84.3 | 84.5 | 84.4 | 84.4 | 84.6 | 84.6 | 84.6 | 84.5 |
| Specific surface area of bright pigment (m²/g) | 2.1 | 2.1 | 2.7 | 2.1 | 7.5 | 7.5 | 7.5 | 7.5 |
| Thickness variation coefficient of metal oxide layer (%) | 17.4 | 17.0 | 19.4 | 17.4 | 24.0 | 24.0 | 24.0 | 24.0 |
| Luminosity L* (−15°) | 97.4 | 84.8 | 84.3 | 84.2 | 138.1 | 123.2 | 89.3 | 74.1 |
| Chromaticness (C*) | 35.10 | 20.70 | 19.60 | 19.90 | 5.39 | 4.46 | 33.80 | 19.40 |

$^{Note1)}$Content of Na$_2$O contained in flaky particles obtained by removing a metal oxide layer from a bright pigment

TABLE 8

|  | Example 15 | Example 16 | Example 17 | Example 18 | Example 19 | Example 20 | Example 21 | Example 22 |
|---|---|---|---|---|---|---|---|---|
| Kind of flaky particle | Glass | Glass | Glass | Glass | Glass | Glass | Alumina | Synthetic mica |
| Refractive index of flaky particle | 1.53 | 1.53 | 1.53 | 1.53 | 1.53 | 1.54 | 1.76 | 1.58 |
| Average thickness of flaky particle (μm) | 0.45 | 0.35 | 0.55 | 0.45 | 0.45 | 0.45 | 0.35 | 0.35 |
| Particle diameter (D50) of flaky particle (μm) | 24.1 | 24.3 | 24.4 | 21.4 | 28.4 | 25.2 | 19.9 | 20.2 |
| Zeta potential of flaky particle (mV) | −19 | −19 | −19 | −19 | −19 | −11 | −13 | −13 |
| Content of $Na_2O$ (% by mass)[Note 1] | 8.7 | 8.7 | 8.7 | 8.7 | 8.7 | 3.7 | 3.9 | 3.9 |
| Kind of metal oxide | Titanium dioxide | Titanium dioxide | Titanium dioxide | Titanium dioxide | Titanium dioxide | Titanium dioxide | Titanium dioxide | Titanium dioxide |
| Particle diameter (D50) of bright pigment (μm) | 24.5 | 24.6 | 24.6 | 21.8 | 28.9 | 25.4 | 20.5 | 20.4 |
| Specific surface area of bright pigment ($m^2/g$) | 1.7 | 1.7 | 1.7 | 1.7 | 1.7 | 2.8 | 2.3 | 2.5 |
| Thickness variation coefficient of metal oxide layer (%) | 7.4 | 7.4 | 7.4 | 7.4 | 7.4 | 18.3 | 18.2 | 18.3 |
| Luminosity L*(−15°) | 143.3 | 143.8 | 141.6 | 142.1 | 143.5 | 143.3 | 140.3 | 140 |
| Chromaticness (C*) | 5.62 | 5.69 | 5.57 | 5.58 | 5.65 | 5.50 | 5.60 | 5.61 |

[Note 1] Content of $Na_2O$ contained in flaky particles obtained by removing a metal oxide layer from a bright pigment

TABLE 9

|  | Comparative Example 5 | Example 23 | Comparative Example 6 | Comparative Example 7 |
|---|---|---|---|---|
| Kind of flaky particle | Glass | Glass | Alumina | Synthetic mica |
| Refractive index of flaky particle | 1.57 | 1.52 | 1.76 | 1.58 |
| Average thickness of flaky particle (μm) | 0.45 | 0.45 | 0.30 | 0.25 |
| Particle diameter (D50) of flaky particle (μm) | 24.2 | 24.5 | 19.7 | 19.2 |
| Zeta potential of flaky particle (mV) | −4 | −23 | −5 | −7 |
| Content of $Na_2O$ (% by mass)[Note 1] | 0.4 | 10.2 | 0.9 | 0.8 |
| Kind of metal oxide | Titanium dioxide | Titanium dioxide | Titanium dioxide | Titanium dioxide |
| Particle diameter (D50) of bright pigment (μm) | 24.4 | 24.7 | 20.3 | 20.1 |
| Specific surface area of bright pigment ($m^2/g$) | 8.7 | 1.7 | 9.3 | 10.5 |
| Thickness variation coefficient of metal oxide layer (%) | 24.0 | 7.4 | 24.2 | 25.3 |
| Luminosity L*(−15°) | 132.5 | 143 | 132.6 | 130.7 |
| Chromaticness (C*) | 5.48 | 5.60 | 5.51 | 5.49 |

[Note 1] Content of $Na_2O$ contained in flaky particles obtained by removing a metal oxide layer from a bright pigment Further, the bright pigments of Examples 1 to 23 and Comparative Examples 1 to 7 were measured for the luminosity L* and the chromaticness (C*) by the following methods, and Table 5 shows the results.

Further, the crystal structure of titanium dioxide in each metal oxide layer of the bright pigments of Examples and Comparative Example 1 were found to be a rutile type by a powder X-ray diffraction method.

<Measurement Method of Particle Size Distribution>

A laser diffraction particle size distribution analyzer (product name: "Microtrac HRA" manufactured by Nikkiso Co., Ltd.) was used for measuring a particle size distribution of flaky particles and a bright pigment. From the measurement results, a particle diameter (D50) corresponding to a 50% volume-cumulative particle diameter from a small particle diameter side was determined.

<Thickness Distribution of Flaky Particles>

A thickness "d" (see FIG. 1) was measured with an electronic microscope for any 100 flaky particles to obtain average thickness.

<Content of $Na_2O$>

0.1 g of flaky particles obtained by removing a metal oxide layer from a bright pigment were weighed precisely and dissolved in 4 ml of perchloric acid ($HClO_4$) and 7.5 ml of hydrofluoric acid. After that, the resultant was solidified by drying and dissolved in 2 ml of hydrochloric acid (1+1). Then, the absorbency of sodium at a wavelength of 589 nm was measured with a flame spectrophotometer. The content of $Na_2O$ contained in flaky particles before the formation of a metal oxide layer was similarly obtained (see Tables 4 to 6).

The amount a(g) of sodium oxide in the sample was calculated by the following expression.

$$a(g) = \text{measurement value (ppm)} \times 10^{-3} \times (100/1000)$$

$$Na_2O\ (\%) = (a/W) \times 100$$

W: Collected amount of bright pigment (g)

<Specific Surface Area of Bright Pigment>

1 g of a bright pigment was weighed precisely and put in a measurement cell and measured for a specific surface area through use of "NOVA1000" manufactured by Yuasa Ionics, Inc.

<Zeta Potential>

A plate sample of the same composition as that of flaky particles and hydrochloric acid aqueous solution of pH 2.0 were prepared in advance, and the zeta potential was measured through use of "ELS-6000" manufactured by Otsuka Electronics Co., Ltd. and a plate sample cell by an electrophoretic light scattering method.

<Thickness of Metal Oxide Layer>

The thickness of a metal oxide layer was measured as follows. A bright pigment embedded in a resin and solidified was ruptured, and a cross-section of the resultant was subjected to a conductive treatment by Pt—Pd coating. The cross-section was observed with an electron microscope, and the thickness of the metal oxide layer was measured. Five particles were observed and each thickness of 10 positions was measured for one particle. A thickness variation coefficient of the metal oxide layer was calculated through use of values of a thickness standard deviation and an average thickness determined from the thickness of the metal oxide layer thus obtained.

<Production of Coating Sample>

78% by mass of an acrylic resin (product name: "Acrydic A-322" manufactured by DIC Corporation), 16% by mass of a butylated melamine resin (product name: "Super Beckamine L-117-60" manufactured by DIC Corporation), and 6% by mass of the bright pigment obtained in each of Examples 1 to 23 and Comparative Examples 1 to 7 were mixed with a stirrer, while the viscosity was adjusted to 13 Pa·s ("Ford cup No. 4/20° C." manufactured by Yasuda Seiki Seisakusho, Ltd.) by adding an appropriate amount of thinner thereto. Thus, a metallic base paint (bright pigment composition) was prepared. The metallic base paint was applied onto a coated plate (coating color: Munsell color system N=9.5 (CIE L*a*b* color system L*=95)) through use of a spray gun ("W-100" manufactured by Anest Iwata Corporation), so that a metallic base coating film was formed thereon.

Subsequently, 72% by mass of an acrylic resin (product name: "Acrydic A-345" manufactured by DIC Corporation) and 28% by mass of a butylated melamine resin (product name: "Super Beckamine L-117-60" manufactured by DIC Corporation) were mixed with a stirrer, while the viscosity was adjusted to 24 Pa·s ("Ford cup No. 4/20° C." manufactured by Yasuda Seiki Seisakusho, Ltd.) by adding thinner thereto. Thus, a clear paint was prepared. The clear paint was applied onto the coated plate having the metallic base coating film formed thereon through use of the spray gun ("W-100" manufactured by Anest Iwata Corporation), followed by baking (at 140° C. for 30 minutes), so that a metallic base layer and a top clear layer were formed thereon. The thickness of the coating film after the baking was such that the metallic base layer was 15 μm thick, and the top clear layer was 30 μm thick.

<Luminosity L*(−15°)>

The brightness in highlight areas of a bright pigment in a metallic base layer was evaluated through use of a multi-angle color & effect control measurement unit (product name: "BYK-mac" manufactured by BYK-Gardner). The metallic base layer containing a bright pigment has high brightness, reflecting light sufficiently in highlight areas, whereas the metallic base layer becomes dark in shade areas. Thus, an angle change in luminosity and tint called "Flop" occurs.

As shown in FIG. 3, a light source 62 is provided at a position of 45° from a direction perpendicular to the surface of a metallic base layer 61 (that is, 45° from a film surface), and the metallic base layer is irradiated with light from an angle of 45°. At an angle shifted by 15° from a direction of regular reflection of incident light (that is, 45° from the film surface) to an opposite direction of the light source, light reflected from the bright pigment becomes maximum. This position is called "−15°". L*a*b* of reflected light having entered a detector 63 was measured. The luminosity L* is preferably 135 or more, more preferably 140 or more.

<Chromaticness C*>

Chromaticness was evaluated as follows. First, a bright pigment was added to an acrylic resin paint (product name: "Acrylic Auto Clear Super" manufactured by Nippon Paint Co., Ltd., solid content: about 30% by mass) and thoroughly mixed by stirring. Then, the mixture was applied onto a contrast ratio measurement paper with an applicator having a gap of 9 mils (9/1000 inches) and dried. The coated plate thus obtained was measured for values of hues a* and b* through use of a chroma meter ("CR400" manufactured by Konica Minolta Inc.), and C* was determined by the following expression. It should be noted that the bright pigment was added so that the content thereof became 10% by mass in the mixture of the acrylic resin paint and the bright pigment. As the value b* is smaller, yellowing is more suppressed and an original color of an acrylic resin is exhibited more. As the value of C* is larger, the chromaticness is higher.

$$C^* = \{(a^*)^2 + (b^*)^2\}^{1/2}$$

As shown in Tables 7 to 9, a coated matter having both high luminosity and high chromaticness can be provided through use of a bright pigment having a thickness variation coefficient of a metal oxide layer of 20% or less.

INDUSTRIAL APPLICABILITY

The bright pigment of the present invention has both high chromaticness and high brightness, and hence can be applied to various applications such as cosmetics.

The invention claimed is:

1. A bright pigment comprising a flaky glass particle and a metal oxide layer covering a surface of the flaky glass particle, wherein the flaky glass particle contains $Na_2O$ in an amount of 7% by mass or more and less than 9% by mass, the metal oxide layer consists essentially of at least one selected from the group consisting of titanium dioxide ($TiO_2$) and reduced titanium dioxide ($TiO_{2-x}$) obtained by reducing titanium dioxide, a crystal phase of the metal oxide layer contains sodium ions, and the metal oxide layer has a thickness variation coefficient of 20% or less, wherein the thickness variation coefficient is a standard deviation of thickness of the metal oxide layer divided by an average thickness of the metal oxide layer.

2. The bright pigment according to claim 1, wherein the bright pigment has a specific surface area of 5.0 m²/g or less.

3. The bright pigment according to claim 1, wherein the bright pigment has a particle diameter of 10 to 300 μm, which is a 50% volume-cumulative particle diameter from a small particle diameter side in a particle size distribution.

4. The bright pigment according to claim 1, wherein the metal oxide layer comprises titanium dioxide and the sodium ions.

5. Cosmetics comprising the bright pigment according to claim 1.

6. A paint composition comprising the bright pigment according to claim 1.

7. A resin composition comprising the bright pigment according to claim 1.

8. A method for producing a bright pigment according to claim 1, the method comprising:
  adding an aqueous solution of a metal compound to a slurry for forming a metal oxide layer containing the flaky glass particle and acid to deposit a hydrate of an oxide of a metal derived from the metal compound on the surface of the flaky glass particle, thereby covering the flaky glass particle with a metal oxide hydrate layer containing the hydrate of the oxide of the metal; and
  of washing and drying the flaky glass particle covered with the metal oxide hydrate layer, and baking the resultant flaky glass particle covered with the metal oxide hydrate layer to form the metal oxide hydrate layer into a metal oxide layer,
  wherein the flaky glass particle to be used for preparing the slurry for forming a metal oxide layer has a zeta potential of −25 mV to −10 mV in hydrochloric acid aqueous solution of pH 2,
  the flaky glass particle covered with the metal oxide layer contains $Na_2O$ in an amount of 7% by mass or more and less than 9% by mass,
  the metal oxide layer consists essentially of at least one selected from the group consisting of titanium dioxide ($TiO_2$) and reduced titanium dioxide ($TiO_{2-x}$) obtained by reducing titanium dioxide,
  a crystal phase of the metal oxide layer contains sodium ions, and
  the metal oxide layer has a thickness variation coefficient of 20% or less, wherein the thickness variation coefficient is a standard deviation of thickness of the metal oxide layer divided by an average thickness of the metal oxide layer.

9. The method for producing a bright pigment according to claim 8, wherein the aqueous solution of the metal compound is a titanium-containing aqueous solution, and
  the titanium-containing solution is an aqueous solution containing at least one kind selected from the group consisting of titanium tetrachloride, titanium trichloride, titanium dichloride, titanium sulfate, titanyl sulfate, titanium nitrate, and titanyl nitrate.

10. The method for producing a bright pigment according to claim 8, wherein a baking temperature is 600° C. or less in the baking the resultant flaky glass particle.

\* \* \* \* \*

UNITED STATES PATENT AND TRADEMARK OFFICE
CERTIFICATE OF CORRECTION

PATENT NO. : 10,544,309 B2
APPLICATION NO. : 14/363695
DATED : January 28, 2020
INVENTOR(S) : Kitamura Page 1 of 1

It is certified that error appears in the above-identified patent and that said Letters Patent is hereby corrected as shown below:

On the Title Page

Page 2, item (56), Column 2, under "Other Publications", Line 36, delete "MicroglasR" and insert -- Microglas® --.

Page 3, item (56), Column 1, under "Other Publications", Lines 6-7, delete "Safety Data Sheet MicroglasR Fineflake MC108OFF, Nippon Sheet Glass Co.,Ltd., Jun. 8, 2015."

In the Specification

Column 3, Line 21, delete "0.2" and insert -- 0.2 μm --.

Column 9, Line 19, delete "85°," and insert -- 85° C., --.

Column 17, Line 53, after "(TiO$_{1.7}$)" insert -- . --.

Column 27, below "TABLE 7", Line 1, delete "$^{Note1)}$Content" and insert -- Note 1) Content --.

Column 29, below "TABLE 8", Line 1, delete "$^{Note1)}$Content" and insert -- Note 1) Content --.

Column 29, below "TABLE 9", Line 1, delete "$^{Note1)}$Content" and insert -- Note 1) Content --.

In the Claims

Column 33, in Claim 8, Line 26, delete "of" before "washing".

Signed and Sealed this
Twenty-first Day of July, 2020

Andrei Iancu
*Director of the United States Patent and Trademark Office*